US009365518B2

(12) United States Patent
deLong et al.

(10) Patent No.: US 9,365,518 B2
(45) Date of Patent: *Jun. 14, 2016

(54) 6-AMINOISOQUINOLINE COMPOUNDS

(71) Applicant: Aerie Pharmaceuticals, Inc., Research Triangle Park, NC (US)

(72) Inventors: Mitchell A. deLong, Chapel Hill, NC (US); Susan M. Royalty, Davis, CA (US); Jill Marie Sturdivant, Chapel Hill, NC (US); Geoffrey Richard Heintzelman, Durham, NC (US)

(73) Assignee: Aerie Pharmaceuticals, Inc., Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/583,439

(22) Filed: Dec. 26, 2014

(65) Prior Publication Data

US 2015/0119419 A1 Apr. 30, 2015

Related U.S. Application Data

(63) Continuation of application No. 13/723,811, filed on Dec. 21, 2012, now Pat. No. 8,921,392, which is a continuation of application No. 13/017,708, filed on Jan. 31, 2011, now Pat. No. 8,357,699, which is a continuation of application No. 11/621,887, filed on Jan. 10, 2007, now Pat. No. 8,455,513.

(51) Int. Cl.
| | | |
|---|---|---|
| C07D 217/02 | (2006.01) |
| C07D 215/38 | (2006.01) |
| C07D 401/02 | (2006.01) |
| A61K 31/47 | (2006.01) |
| C07D 217/04 | (2006.01) |
| C07D 401/12 | (2006.01) |

(52) U.S. Cl.
CPC ............ *C07D 217/04* (2013.01); *C07D 215/38* (2013.01); *C07D 217/02* (2013.01); *C07D 401/12* (2013.01)

(58) Field of Classification Search
None
See application file for complete search history.

(56) References Cited

U.S. PATENT DOCUMENTS

| | | | |
|---|---|---|---|
| 4,146,637 A | 3/1979 | Metz et al. |
| 4,337,256 A | 6/1982 | Suzuki et al. |
| 4,456,757 A | 6/1984 | Hidaka et al. |
| 4,709,032 A | 11/1987 | Hidaka et al. |
| 4,911,928 A | 3/1990 | Wallach |
| 4,954,512 A | 9/1990 | Oguro et al. |
| 5,508,288 A | 4/1996 | Forbes et al. |
| 5,519,036 A | 5/1996 | Himmelsbach et al. |
| 5,798,380 A | 8/1998 | Kaufman et al. |
| 5,891,646 A | 4/1999 | Barak et al. |
| 6,110,693 A | 8/2000 | Barak et al. |
| 6,110,912 A | 8/2000 | Kaufman et al. |
| 6,362,177 B1 | 3/2002 | Shiota et al. |
| 6,586,425 B2 | 7/2003 | Kaufman et al. |
| 6,699,891 B1 | 3/2004 | Kawanishi et al. |
| 6,787,534 B2 | 9/2004 | Haneda et al. |
| 7,268,143 B2 | 9/2007 | Jagtap et al. |
| 7,329,684 B2 | 2/2008 | Mjalli et al. |
| 7,345,158 B2 | 3/2008 | Egashira et al. |
| 7,361,678 B2 | 4/2008 | Mjalli et al. |
| 7,374,891 B2 | 5/2008 | Shahbaz |
| 7,378,498 B2 | 5/2008 | Worley et al. |
| 7,470,787 B2 | 12/2008 | deLong et al. |
| 7,671,205 B2 | 3/2010 | deLong et al. |
| 8,034,943 B2 | 10/2011 | deLong et al. |
| 8,357,699 B2 | 1/2013 | deLong et al. |
| 8,394,826 B2 | 3/2013 | deLong et al. |
| 8,450,344 B2 | 5/2013 | deLong et al. |
| 8,455,513 B2 | 6/2013 | deLong et al. |
| 8,455,514 B2 | 6/2013 | deLong et al. |
| 8,455,647 B2 | 6/2013 | deLong et al. |
| 8,716,310 B2 | 5/2014 | deLong et al. |
| 8,759,388 B2 | 6/2014 | deLong et al. |
| 8,809,326 B2 | 8/2014 | Bosanac et al. |
| 8,871,757 B2 | 10/2014 | deLong et al. |
| 8,921,392 B2 | 12/2014 | deLong et al. |
| 9,096,569 B2 | 8/2015 | deLong et al. |
| 2004/0091946 A1 | 5/2004 | Oakley et al. |
| 2004/0176462 A1 | 9/2004 | Kawanishi et al. |
| 2005/0032125 A1 | 2/2005 | Oakley et al. |
| 2005/0176712 A1 | 8/2005 | Wakabayashi et al. |
| 2005/0245509 A1 | 11/2005 | Nakajima et al. |

(Continued)

FOREIGN PATENT DOCUMENTS

| | | |
|---|---|---|
| EP | 0109023 | 5/1984 |
| EP | 0232569 | 8/1987 |

(Continued)

OTHER PUBLICATIONS

United States Patent Office Action for U.S. Appl. No. 14/461,597 dated Jan. 30, 2015 (19 pages).
Gingras et al., "In Synthesis and evaluation of 4-(1-aminoalkyl)-N-(4-pyridyl)-cyclohexanecarboxamides as Rho-kinase inhibitors and neurite outgrowth promoters," Bioorganic & Medicinal Chemistry Letters, 2004, vol. 14, pp. 4931-4934.
Olson, "Application for ROCK kinase inhibition," Current Opinion in Cell Biology, 2008, vol. 20, pp. 242-248.
Yamashita et al., "The therapeutic effects of Rho-Rock inhibitors on CNS disorder," Therapeutics and Clinical Risk Management, 2008, vol. 4, pp. 605-615.

(Continued)

*Primary Examiner* — Zinna Northington Davis
(74) *Attorney, Agent, or Firm* — Michael Best & Friedrich LLP

(57) ABSTRACT

6-Amino isoquinoline compounds are provided that influence, inhibit or reduce the action of a kinase. Pharmaceutical compositions including therapeutically effective amounts of the 6-aminoisoquinoline compounds and pharmaceutically acceptable carriers are also provided. Various methods using the compounds and/or compositions to affect disease states or conditions such as cancer, obesity and glaucoma are also provided.

21 Claims, No Drawings

(56) References Cited

U.S. PATENT DOCUMENTS

| | | |
|---|---|---|
| 2005/0282805 A1 | 12/2005 | Hangeland et al. |
| 2006/0270670 A1 | 11/2006 | Chew et al. |
| 2007/0111983 A1 | 5/2007 | Fong |
| 2007/0123561 A1 | 5/2007 | Lee et al. |
| 2007/0129404 A1 | 6/2007 | Hagihara et al. |
| 2007/0135499 A1 | 6/2007 | deLong et al. |
| 2007/0149473 A1 | 6/2007 | Chatterton et al. |
| 2007/0149548 A1 | 6/2007 | Hellberg et al. |
| 2007/0167444 A1 | 7/2007 | Kuramochi et al. |
| 2007/0238741 A1 | 10/2007 | Nagarathnam et al. |
| 2008/0021026 A1 | 1/2008 | Kahraman et al. |
| 2008/0021217 A1 | 1/2008 | Borchardt |
| 2008/0058384 A1 | 3/2008 | Lee et al. |
| 2008/0096238 A1 | 4/2008 | Sharif et al. |
| 2008/0125427 A1 | 5/2008 | Sehon et al. |
| 2008/0139595 A1 | 6/2008 | Schirok et al. |
| 2008/0153799 A1 | 6/2008 | Laurent et al. |
| 2008/0153813 A1 | 6/2008 | Chen et al. |
| 2008/0194584 A1 | 8/2008 | Birault et al. |
| 2008/0275029 A1 | 11/2008 | Berdini et al. |
| 2009/0005321 A1 | 1/2009 | Zimmer et al. |
| 2009/0069371 A1 | 3/2009 | deLong et al. |
| 2010/0093790 A1 | 4/2010 | deLong et al. |
| 2010/0105650 A1 | 4/2010 | Plettenburg et al. |
| 2012/0135984 A1 | 5/2012 | deLong et al. |
| 2014/0187617 A1 | 7/2014 | deLong et al. |
| 2014/0357652 A1 | 12/2014 | Bosanac et al. |
| 2015/0175549 A1 | 6/2015 | deLong et al. |

FOREIGN PATENT DOCUMENTS

| | | |
|---|---|---|
| EP | 0389995 | 10/1990 |
| EP | 0482939 | 4/1992 |
| EP | 1541151 | 6/2005 |
| EP | 1550660 | 7/2005 |
| JP | 2005227441 | 8/2005 |
| JP | 2007236388 | 9/2007 |
| JP | 2007246466 | 9/2007 |
| WO | WO 93/18028 | 9/1993 |
| WO | WO 00/76970 | 12/2000 |
| WO | WO 01/37826 | 5/2001 |
| WO | WO 01/47891 | 7/2001 |
| WO | WO 01/53268 | 7/2001 |
| WO | WO 01/53274 | 7/2001 |
| WO | WO 01/56607 | 8/2001 |
| WO | WO 02/22576 | 3/2002 |
| WO | WO 02/32864 | 4/2002 |
| WO | WO 02/085857 | 10/2002 |
| WO | WO 02/085859 | 10/2002 |
| WO | WO 03/064397 | 8/2003 |
| WO | WO 03/073999 | 9/2003 |
| WO | WO 03/080578 | 10/2003 |
| WO | WO 2004/029045 | 4/2004 |
| WO | WO 2004/078747 | 9/2004 |
| WO | WO 2005/020921 | 3/2005 |
| WO | WO 2005/035503 | 4/2005 |
| WO | WO 2005/037257 | 4/2005 |
| WO | WO 2006/041119 | 4/2006 |
| WO | WO 2006/051290 | 5/2006 |
| WO | WO 2006/062982 | 6/2006 |
| WO | WO 2006/076706 | 7/2006 |
| WO | WO 2007/008926 | 1/2007 |
| WO | WO 2007/008942 | 1/2007 |
| WO | WO 2007/060028 | 5/2007 |
| WO | WO 2007/065916 | 6/2007 |
| WO | WO 2007/076360 | 7/2007 |
| WO | WO 2007/076367 | 7/2007 |
| WO | WO 2007/100880 | 9/2007 |
| WO | WO 2007/142323 | 12/2007 |
| WO | WO 2008/011557 | 1/2008 |
| WO | WO 2008/011560 | 1/2008 |
| WO | WO 2008/016016 | 2/2008 |
| WO | WO 2008/036459 | 3/2008 |
| WO | WO 2008/036540 | 3/2008 |
| WO | WO 2008/049000 | 4/2008 |
| WO | WO 2008/049919 | 5/2008 |
| WO | WO 2008/054599 | 5/2008 |
| WO | WO 2008/077057 | 6/2008 |
| WO | WO 2008/077550 | 7/2008 |
| WO | WO 2008/077551 | 7/2008 |
| WO | WO 2008/077552 | 7/2008 |
| WO | WO 2008/077553 | 7/2008 |
| WO | WO 2008/077554 | 7/2008 |
| WO | WO 2008/077555 | 7/2008 |
| WO | WO 2008/077556 | 7/2008 |
| WO | WO 2008/079880 | 7/2008 |
| WO | WO 2008/079945 | 7/2008 |
| WO | WO 2008/086269 | 7/2008 |
| WO | WO 2008/124665 | 10/2008 |
| WO | WO 2009/091898 | 7/2009 |
| WO | WO 2010/011853 | 1/2010 |
| WO | WO 2010/126626 | 11/2010 |
| WO | WO 2010/127329 | 11/2010 |
| WO | WO 2010/127330 | 11/2010 |
| WO | WO 2012/105674 | 8/2012 |

OTHER PUBLICATIONS

Rashid et al., "Development of Rho-kinase inhibitors for cardiovascular medicine," Trends in Pharmacological Science, 2007, vol. 28, pp. 296-302.

Pardridge, "The Blood-Brain Barrier: Bottleneck in Brain Drug development," J. Am. Soc. Exper. NeuroTherapeutics, 2005, vol. 2, p. 3-14.

Banker, G.S. et al., Modern Pharmaceutics, Marcel Dekker, Inc., New York, (1979) Chapters 9 and 10.

Bird, G.J. et al., "N-methyl as a bioisostere for the oxygen link between the aromatic rings of aryloxyphenoxypropionate herbicides," Bioorg. Med. Chem. Lett. (1997) 7:1489-1492.

Blough BE, Keverline KI, Nie Z, Navarro H, Kuhar MJ, Carroll FI (2002). "Synthesis and transporter binding properties of 3beta-[4'-(phenylalkyl, phenylalkenyl, and phenylalkynyl) phenyltropane]-2beta-carboxylic acid methyl esters: evidence of a remote phenyl binding domain on the dopamine transporter". J. Med. Chem. 45 (18):4029-37.

C.T.F.A. Cosmetic Ingredient Handbook, "Surfactants—Emulsifying Agents", Second Edition, The Cosmetic, Toiletry, and Fragrance Association, New York, Wenninger, J.A. et al., eds. (1992) 587-592.

Calmes et al., Eur. J. Org. Chem. 2000, 2459-2466.

Capdeville, R. et al., "Glivec (STI571, IMATINIB), A Rationally Developed, Targeted Anticancer Drug", Nature Reviews Drug Discovery (2002) 1:493-502.

Chen, P. et al., "Identification of novel and potent isoquinoline aminooxazole-based IMPDH inhibitors," Bioorg. Med. Chem. Lett. (2003) 13(7):1345-1348.

Cheung, S.T. et al. Can. J. Chem. 1977, 55,906-910.

Dancey, J. et al., "Issues and Progress with Protein Kinase Inhibitors for Cancer Treatment", Nature Reviews Drug Discovery (2003) 2:296-313.

Dorwald, F.Z., Side Reactions in Organic Synthesis. A Guide to Successful Synthesis Design, Wiley-VCH, Weinheim (2005) IX of Preface and 1-15.

Dowton et al., "Influence of Liposomal Composition on Topical Delivery of Encapsulated Cyclosporin A", S.T.P. Pharma Sciences, vol. 3, pp. 404-407 (1993).

Foye, Foye's Principles of Medicinal Chemistry, 5th Edition (2002) Lippencott, Williams, Wilkins, p. 59-63.

G.E. Torres, R.R. Gainetdinov and M.G. Caron (2003). "Plasma membrane monoamine transporters: structure, regulation and function". Nat. Rev. Neurosci. 4 (1): 13-25.

Hackam, A.S. et al., "The Wnt Signaling Pathway in Retinal Degenerations", IUBMB Life (2005) 57(6):381-388.

Hazeldine, S.T. et al., "II. Synthesis and biological evaluation of some bioisosteres and cogeners of the antitumour agent, 2{4[7-chloro-2-quinoxalinyl)oxy]phenoxy}propionic acid (XK469)," J. Med. Chem. (2002) 45:3130-3137.

He R, Kurome T, Giberson KM, Johnson KM, Kozikowski AP (2005). "Further structure-activity relationship studies of piperidine-based monoamine transporter inhibitors: effects of piperidine ring

(56) References Cited

OTHER PUBLICATIONS stereochemistry on potency. Identification of norepinephrine transporter selective ligands and broad-spectrum transporter inhibitors". J. Med. Chern. 48 (25): 7970-9.
Helal, C.J. et al., "Discovery and SAR of 2-aminothiazole inhibitors of cyclin-dependent kinase 5/p25 as a potential treatment for Alzheimer's disease," Bioorg. Med. Chem. (2004) 14(22):5521-5525.
Hu, E. et al., "Rho kinase as potential therapeutic target for cardiovascular diseases: opportunities and challenges," Exp. Opin. Ther. Targets (2005) 9:715-736.
Inouye, Y. et al., "The Absolute Configurations of Trans-1,2-Cyclopropanedicarboxylic Acid and Trans-2-Phenylcyclopropanecarboxylic Acid", Int'l. J. Org. Chem. (1964) 20(5):1695-1699.
Ito, N. et al., "A medium-term rat liver bioassay for rapid in vivo detection of carcinogenic potential of chemicals," Cancer Science, Jan. 2003, vol. 94, No. 1, pp. 3-8.
Karaman, M.W. et al., "A quantitative analysis of kinase inhibitor selectivity," Nature Biotech. (2008) 26(1):127-132.
Liljebris, C. et al., "Derivatives of 17-Phenyl-18,19,20-trinorprostaglandin F2α Isopropyl Ester: Potential Antiglaucoma Agents," J. Med. Chem. (1995) 38(2):289-304.
Loge, C; Siomboing, X et al. J, of Enzy Inhib & Med Chem, 2003,18,127-128.
Matsui, T. et al., "Novel 5-HT3 antagonists. Isoquinolinones and 3-aryl-2-pyridones," J. Med. Chem. (1992) 35:3307-3319.
McCutcheon's, "Emulsifiers & Detergents", North American Edition (1994) vol. 1:236-239.
Nakanishi et al. FEBS Letters 368, (1995) 411-414.
Oakley, R.H. et al. "The Cellular Distribution of Fluorescently Labeled Arrestins Provides a Robust, Sensitive and Universal Assay for Screening G Protein-Coupled Receptors," Assay and Drug Development Technologies (2002) 1(1-1):21-30.
Parang, K. et al., "Design strategies for protein kinase inhibitors," Curr. Opin. in Drug Disc. & Dev. (2004) 7(5):617-629.
Penmetsa, K.V. et al., "Development of Reversed-Phase Chiral HPLC Methods Using Mass Spectrometry Compatible Mobile Phases", J. Liquid Chroma. Rel. Tech. (2000) 23(6-10):831-839.
Penn, R.B. et al., "Pharmacological Inhibition of Protein Kinases in Intact Cells: Antagonism of Beta Adrenergic Receptor Ligand Binding by H-89 Reveals Limitations of Usefulness." J. Pharm. Exp. Ther. (1999) 288(2):428-437.
Pharmasolve (N-Methyl-2-Pyrrolidone) product spcification, International Specialty Products, 2000, 10 pages.
Shankar, G. et al., "Protein-kinase-specific inhibitors block Langerhans' cell migration by inhibiting interleukin-1α release", Immunology (1999) 96:230-235.
Stirewalt, D.L. et al., "The Role of FLT3 in Haematopoietic Malignancies", Nature Reviews Cancer (2003) 3:650-665.
STN Registry Database entry for CAS RN 309903-43-6, Published in database Dec. 20, 2000.
Tamura, M., et al., "Development of specific Rho-kinase inhibitors and their clinical application," Biochimica et Biophysica Acta, 2005, vol. 1754, pp. 245-252.
Van Muijlwijk-Koezen et al., "A novel class of adenosine A3 receptor-ligands. 2. Structure affinity profile of a series of isoquinoline and quinazoline compounds," J. Med. Chem. (1998) 41:3994-4000.
Wallach and Philippot, "New Type of Lipid Vesicle: Novasome®", Liposome Technology, vol. 1, pp. 141-156 (1993).
Webster, F.X. et al., "Following the Course of Resolution of Carboxylic Acids by 13C NMR Spectrometry of Amine Salts" J. Org. Chem. (1982) 47(26):5225-5226.
Westaway, S.M. et al., "N-tetrahydroquinolinyl, N-quinolinyl and N-isoquinolinyl biaryl carboxamides as antagonists of TRPV1," Biorg. Med. Chem. Lett. (2006) 16:4533-4536.
Westra, J. et al., "p38 Mitogen-Activated Protein Kinase (MAPK) in Rheumatoid Arthritis", Mini-Reviews in Medicinal Chemistry (2006) 6(8):867-874.

Jacobs, M. et al., "The structure of dimeric ROCK I reveals the mechanism for ligand selectivity," J. Bio. Chem., 2006, pp. 260-268, published on Jan. 6, 2006.
Meanwell, "Synopsis of some recent tactical application of bioisosteres in drug design," J. Med. Chem., 2011, vol. 54, pp. 2529-2591.
United States Office Action for U.S. Appl. No. 11/485,182 dated Apr. 16, 2009 (13 pages).
United States Office Action for U.S. Appl. No. 12/274,887 dated Jun. 16, 2009 (11 pages).
United States Patent Office Action for U.S. Appl. No. 12/639,670 dated Jan. 31, 2011 (8 pages).
United States Patent Office Action for U.S. Appl. No. 12/639,670 dated Jul. 27, 2011 (5 pages).
United States Patent Office Action for U.S. Appl. No. 11/621,887 dated May 18, 2010 (8 pages).
United States Patent Office Action for U.S. Appl. No. 11/621,887 dated Oct. 29, 2010 (14 pages).
United States Patent Office Action for U.S. Appl. No. 13/017,708 dated Apr. 3, 2012 (11 pages).
United States Patent Office Notice of Allowance for U.S. Appl. No. 13/017,708 dated Sep. 17, 2012 (8 pages).
United States Patent Office Notice of Allowance for U.S. Appl. No. 13/017,708 dated Oct. 23, 2012 (7 pages).
United States Patent Office Notice of Allowability for U.S. Appl. No. 13/017,708 dated Dec. 12, 2012 (5 pages).
United States Patent Office Notice of Allowance for U.S. Appl. No. 11/621,887 dated Feb. 27, 2013 (8 pages).
United States Patent Office Action for U.S. Appl. No. 13/723,811 dated Jan. 27, 2014 (8 pages).
United States Patent Office Action for U.S. Appl. No. 13/723,811 dated Jun. 17, 2014 (6 pages).
United States Patent Office Notice of Allowance for U.S. Appl. No. 13/723,811 dated Aug. 19, 2014 (11 pages).
United States Office Action for U.S. Appl. No. 11/621,892 dated Aug. 8, 2008 (9 pages).
United States Office Action for U.S. Appl. No. 11/621,892 dated Mar. 9, 2009 (6 pages).
United States Patent Office Action for U.S. Appl. No. 12/701,963 dated May 10, 2011 (3 pages).
United States Patent Office Action for U.S. Appl. No. 13/230,105 dated Mar. 5, 2012 (8 pages).
United States Patent Office Final Rejection for U.S. Appl. No. 13/230,105 dated Jul. 9, 2012 (11 pages).
United States Patent Office Notice of Allowance for U.S. Appl. No. 13/230,105 dated Mar. 19, 2013 (5 pages).
United States Patent Office Action for U.S. Appl. No. 12/009,326 dated Feb. 3, 2011 (8 pages).
United States Patent Office Notice of Allowance for U.S. Appl. No. 12/009,326 dated Jan. 6, 2012 (5 pages).
United States Patent Office Notice of Allowance for U.S. Appl. No. 12/009,326 dated Feb. 25, 2013 (8 pages).
United States Patent Office Action for U.S. Appl. No. 12/704,822 dated Apr. 30, 2012 (34 pages).
United States Patent Office Final Rejection for U.S. Appl. No. 12/704,822 dated Jan. 16, 2013 (16 pages).
United States Patent Office Action for U.S. Appl. No. 12/704,822 dated Oct. 10, 2013 (11 pages).
United States Patent Office Action for U.S. Appl. No. 12/704,822 dated May 8, 2014 (13 pages).
United States Patent Office Notice of Allowance for U.S. Appl. No. 12/704,822 dated Sep. 9, 2014 (11 pages).
United States Patent Office Advisory Action for U.S. Appl. No. 11/856,740 dated Feb. 10, 2011 (3 pages).
United States Patent Office Action for U.S. Appl. No. 11/856,740 dated Dec. 6, 2010 (12 pages).
United States Patent Office Action for U.S. Appl. No. 11/856,740 dated Jun. 29, 2010 (10 pages).
United States Patent Office Action for U.S. Appl. No. 12/180,259 dated Jul. 5, 2011 (11 pages).
United States Patent Office Notice of Allowance for U.S. Appl. No. 12/180,259 dated Dec. 19, 2011 (6 pages).

(56) References Cited

OTHER PUBLICATIONS

United States Patent Office Notice of Allowance for U.S. Appl. No. 13/442,263 dated Dec. 19, 2012 (13 pages).
United States Patent Office Notice of Allowance for U.S. Appl. No. 13/442,263 dated Feb. 25, 2013 (8 pages).
United States Patent Office Notice of Allowance for U.S. Appl. No. 13/442,263 dated Jun. 12, 2013 (8 pages).
United States Patent Office Final Rejection for U.S. Appl. No. 13/442,263 dated Dec. 6, 2013 (8 pages).
United States Patent Office Notice of Allowance for U.S. Appl. No. 13/442,263 dated Apr. 15, 2014 (8 pages).
United States Patent Office Action for U.S. Appl. No. 14/273,895 dated Aug. 20, 2014 (8 pages).
United States Patent Office Action for U.S. Appl. No. 14/273,895 dated Dec. 24, 2014 (7 pages).
United States Patent Office Action for U.S. Appl. No. 13/318,457 dated Jun. 6, 2013 (12 pages).
United States Patent Office Final Rejection for U.S. Appl. No. 13/318,457 dated Nov. 27, 2013 (13 pages).
United States Patent Office Action for U.S. Appl. No. 12/694,965 dated May 17, 2012 (13 pages).
United States Patent Office Notice of Allowance for U.S. Appl. No. 12/694,965 dated Nov. 2, 2012 (8 pages).
United States Patent Office Notice of Allowance for U.S. Appl. No. 12/694,965 dated Nov. 19, 2012 (4 pages).
United States Patent Office Notice of Allowance for U.S. Appl. No. 13/768,594 dated Oct. 29, 2013 (7 pages).
United States Patent Office Action for U.S. Appl. No. 13/768,594 dated Jul. 10, 2013 (14 pages).
United States Patent Office Action for U.S. Appl. No. 14/138,592 dated Jul. 28, 2014 (17 pages).
United States Patent Office Action for U.S. Appl. No. 14/138,592 dated Dec. 9, 2014 (13 pages).
United States Patent Office Action for U.S. Appl. No. 11/856,740 dated Aug. 16, 2013 (14 pages).
United States Patent Office Notice of Allowance for U.S. Appl. No. 11/856,740 dated Apr. 1, 2014 (8 pages).
Partial International Search for Application No. PCT/US2009/031117 dated Apr. 16, 2009 (4 pages).
International Search Report and Written Opinion for Application No. PCT/US2006/026976 dated Feb. 15, 2007 (14 pages).
International Search Report for Application No. PCT/US2006/026947 dated Nov. 17, 2006 (4 pages).
International Preliminary Examination Report for Application No. PCT/US2006/026947 dated Jan. 24, 2008 (10 pages).
International Search Report for Application No. PCT/US08/50374 dated Oct. 28, 2008 (7 pages).
International Preliminary Report on Patentability for Application No. PCT/US08/50374 dated Jul. 14, 2009 (12 pages).
International Search Report and Written Opinion for Application No. PCT/US2009/031117 dated Sep. 24, 2009 (13 pages).
Invitation to Pay Additional Fees and Partial International Search Report for International Application No. PCT/US2009/051569 dated Oct. 15, 2009 (4 pages).
International Search Report and Written Opinion for Application No. PCT/US2009/051569 dated May 20, 2010 (11 pages).
International Search Report and Written Opinion for Application No. PCT/US2010/33316 dated Jul. 14, 2010 (10 pages).
International Search Report and Written Opinion for Application No. PCT/US2010/33317 dated Aug. 17, 2010 (10 pages).
International Search Report and Written Opinion for Application No. PCT/US2010/022246 dated Nov. 10, 2010 (7 pages).
International Search Report and Written Opinion for Application No. PCT/US2007/078343 dated Apr. 3, 2008 (12 pages).
European Patent Office Action for Application No. 08713603.2 dated Aug. 14, 2012 (3 pages).
European Patent Office Action for Application No. 08713603.2 dated Nov. 21, 2013 (4 pages).
Examination Report from the Australian Patent Office for Application No. 2008205047 dated Nov. 26, 2012 (6 pages).
Japanese Patent Office Action for Application No. 2009-545622 dated Mar. 1, 2013 (8 pages—Including English Translation).
Japanese Patent Office Action for Application No. 2009-545622 dated Oct. 23, 2013 (8 pages—Including English Translation).
Anonymous, "Aerie Pharmaceuticals, Inc. Gets Good News on Glaucoma Treatment" (Feb. 11, 2012) Retrieved from the Internet: URL:http://www.biospace.com.
Helzner, "Bright New Ideas in Glaucoma Treatment" (2013) Retrieved from the Internet: URL:http://mydigimag.rrd.com.
deLong et al., "Discovery and SAR of a Class of Oculary-active Compounds Displaying a Dual Mechanism of Activity for the Treatment of Glaucoma" (May 6, 2012) Retrieved from the Internet: URL:http://www.aeriepharma.com.
Berge et al, 1977, "Pharmaceutically Acceptable Salts." J. Pharm. Sci. vol. 66, pp. 1-19.
United States Patent Office Notice of Allowance for U.S. Appl. No. 14/273,895 dated Apr. 1, 2015 (8 pages).
International Search Report and Written Opinion for Application No. PCT/US2014/029335, dated Jul. 2, 2014 (11 pages).
United States Patent Office Action for Application No. 14/641,962 dated Sep. 22, 2015 (16 pages).
United States Patent Office Action for U.S. Appl. No. 14/754,787 dated Oct. 30, 2015 (20 pages).
United States Patent Office Action for U.S. Appl. No. 14/213,940 dated Oct. 29, 2015 (33 pages).
United States Patent Office Action for U.S. Appl. No. 14/213,961 dated Oct. 30, 2015 (37 pages).
"Cancer", MedlinePlus (retrieved Jul. 6, 2007) 10 pages, http://www.nlm.nih.gov/medlineplus/cancer.html.
Golub, T.R. et al., "Molecular classification of cancer: class discovery and class prediction by gene expression monitoring," Science (1999) 286:531-537.
Lala, P.K. et al., "Role of nitric oxide in tumor progression: lessons from experimental tumors," Cancer and Metastasis Reviews (1998) 17:91-106.
United States Patent Office Action for U.S. Appl. No. 14/790,376 dated Jan. 22, 2016 (14 pages).

6-AMINOISOQUINOLINE COMPOUNDS

CROSS-REFERENCE TO RELATED APPLICATIONS

This application is a continuation of prior application Ser. No. 13/723,811, filed Dec. 21, 2012, now U.S. Pat. No. 8,921,392, which is a continuation of prior application Ser. No. 13/017,708, filed Jan. 31, 2011, now U.S. Pat. No. 8,357,699, which is a continuation of prior application Ser. No. 11/621,887, filed Jan. 10, 2007, now U.S. Pat. No. 8,455,513, each of which is incorporated herein by reference in its entirety.

FIELD OF THE INVENTION

The present invention relates to 6-aminoisoquinoline compounds that affect the function of kinases in a cell and that are useful as therapeutic agents or with therapeutic agents. In particular, these compounds are useful in the treatment of eye diseases such as glaucoma and for diseases characterized by abnormal growth, such as cancers.

BACKGROUND

A variety of hormones, neurotransmitters and biologically active substances control, regulate or adjust the functions of living bodies via specific receptors located in cell membranes. Many of these receptors mediate the transmission of intracellular signals by activating guanine nucleotide-binding proteins (G proteins) to which the receptor is coupled. Such receptors are generically referred to as G-protein coupled receptors (GPCRs) and include, among others, α-adrenergic receptors, β-adrenergic receptors, opioid receptors, cannabinoid receptors and prostaglandin receptors. The effect of these receptors is not direct but mediated by a host of intracellular proteins. The importance of these secondary, or "downstream" proteins is only now being recognized and investigated as potential intervention points in disease states. One of the most important classes of these downstream proteins is the "kinase" class.

The various kinases play an important role in the regulation of various physiological functions. By way of example, kinases have been implicated in a number of disease states, including, but not limited to: cardiac indications such as angina pectoris, essential hypertension, myocardial infarction, supraventricular and ventricular arrhythmias, congestive heart failure, atherosclerosis, renal failure, diabetes, respiratory indications such as asthma, chronic bronchitis, bronchospasm, emphysema, airway obstruction, upper respiratory indications such as rhinitis, seasonal allergies, inflammatory disease, inflammation in response to injury, rheumatoid arthritis. The importance of p38 MAPK inhibitors as new drugs for rheumatoid arthritis is reflected by the large number of compounds that has been developed over the last years (J. Westra and P. C. Limburg Mini-Reviews in Medicinal Chemistry Volume 6, Number 8, August 2006) Other conditions include chronic inflammatory bowel disease, glaucoma, hypergastrinemia, gastrointestinal indications such as acid/peptic disorder, erosive esophagitis, gastrointestinal hypersecretion, mastocytosis, gastrointestinal reflux, peptic ulcer, Zollinger-Ellison syndrome, pain, obesity, bulimia nervosa, depression, obsessive-compulsive disorder, organ malformations (for example, cardiac malformations), neurodegenerative diseases such as Parkinson's Disease and Alzheimer's Disease, multiple sclerosis, Epstein-Barr infection and cancer (Nature Reviews Drug Discovery 1, 493-502 2002). In other disease states, the role of kinases is only now becoming clear.

The retina is a complex tissue composed of multiple interconnected cell layers, highly specialized for transforming light and color into electrical signals perceived by the brain. Damage or death of the primary light-sensing cells, the photoreceptors, results in devastating effects on vision. Despite the identification of numerous mutations that cause inherited retinal degenerations, the cellular and molecular mechanisms leading from the primary mutations to photoreceptor apoptosis are not well understood, but may involve the wnt pathway (AS Hackam The Wnt Signaling Pathway in Retinal Degeneration IUBMB Life Volume 57, Number 6/June 2005).

The success of the tyrosine-kinase inhibitor STI571 (Gleevec) in the treatment of chronic myelogenous leukaemia (Nature Reviews Drug Discovery 2, 296-313 2003) has spurred considerable efforts to develop other kinase inhibitors for the treatment of a wide range of other cancers (Nature Reviews Cancer 3, 650-665 2003). The balance between the initiation and the inactivation of the intracellular signals regulates the intensity and duration of the response of the receptors to stimuli such as agonists. When desensitization occurs, the mediation or regulation of the physiological function mediated or regulated by the G proteins to which the receptors are coupled is reduced or prevented. For example, when agonists are administered to treat a disease or condition by activation of certain receptors, the receptors become desensitized from the action of the GRKs such that agonist administration may no longer result in therapeutic activation of the appropriate receptors. At that point, administration of the agonist no longer enables sufficient or effective control of or influence on the disease or condition intended to be treated.

In view of the role of kinases in many disease states, there is an urgent and continuing need for ligands which inhibit or modulate the activity of kinases. Without wishing to be bound by theory, it is thought that modulation of the activity of kinases by the compounds of the present invention is responsible for their beneficial effects.

SUMMARY

In a first aspect of the invention, a compound is provided according to Formula (I):

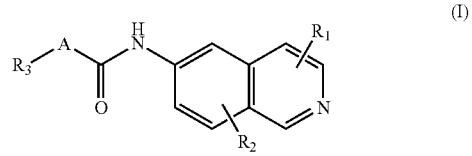

wherein A is —CH$_2$NH—,

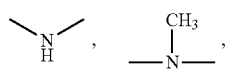

—SCH$_2$—, —CH$_2$S(O)—, —CH$_2$S(O)(O)—, —S(O)CH$_2$—, —S(O)(O)CH$_2$—, —CH$_2$CH$_2$—, —CH(R$_{10}$)CH$_2$—, —CH$_2$CH(R$_{10}$), —CH═CH—,

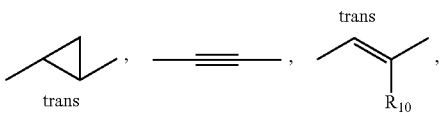 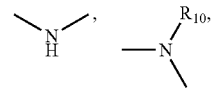

and bond;

wherein R₁₀ is hydrogen, unsubstituted $C_1$-$C_4$ alkyl, $C_1$-$C_4$ alkenyl, $C_1$-$C_4$ alkynyl, or amino;

wherein $R_1$, and $R_2$ are, independently, hydrogen, hydroxyl, halogen, $C_1$-$C_4$ alkyl, $C_2$-$C_4$ alkenyl, $C_2$-$C_4$ alkynyl, amino, nitro, cyano, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl or $C_1$-$C_4$ carboxyl; and wherein $R_3$ is hydrogen, halogen, alkyl, alkenyl, alkynyl, alkoxy, amino, cyano, cycloalkyl, heterocycloalkyl, aryl, $C_1$-$C_4$ alkyl aryl, heteroaryl, $C_1$-$C_4$ alkyl heteroaryl, carbonyl, carbonylamino, thioalkyl, sulfonyl, sulfonylamino, acyl, or carboxyl.

In a second aspect, a compound is provided according to Formula II:

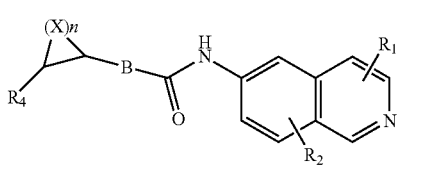

(II)

wherein $R_1$ and $R_2$ are, independently, hydrogen, hydroxyl, halogen, $C_1$-$C_4$ alkyl, $C_2$-$C_4$ alkenyl, $C_2$-$C_4$ alkynyl, amino, nitro, cyano, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl or $C_1$-$C_4$ carboxyl;

wherein $R_4$ is hydrogen, halogen, alkyl, alkenyl, alkynyl, alkoxy, amino, cyano, cycloalkyl, heterocycloalkyl, aryl, $C_1$-$C_4$ alkyl aryl, heteroaryl, $C_1$-$C_4$ alkyl heteroaryl, carbonyl, carbonylamino, thioalkyl, sulfonyl, sulfonylamino, acyl, or carboxyl; and wherein B is a chain containing from 0 to 3 member atoms, X represents n independently chosen member atoms which together form a ring structure and n is an integer from about 0 to about 5.

In another aspect, a compound is provided according to Formula III:

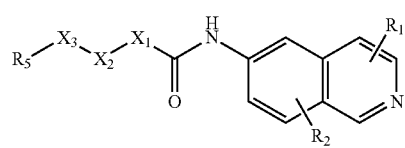

(III)

wherein one of $X_1$, $X_2$ and $X_3$ is independently selected from $CH_2$, O, S, S(O), S(O)(O),

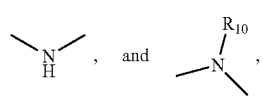

and the other two of $X_1$, $X_2$ and $X_3$ are independently selected from $CH_2$, O, S, S(O), S(O)(O), wherein $R_1$, and $R_2$ are, independently, hydrogen, hydroxyl, halogen, $C_1$-$C_4$ alkyl, $C_2$-$C_4$ alkenyl, $C_2$-$C_4$ alkynyl, amino, nitro, cyano, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl and $C_1$-$C_4$ carboxyl; and wherein $R_5$ and $R_{10}$ are independently hydrogen, halogen, alkyl, alkenyl, alkynyl, alkoxy, amino, cyano, cycloalkyl, heterocycloalkyl, aryl, $C_1$-$C_4$ alkyl aryl, heteroaryl, $C_1$-$C_4$ alkyl heteroaryl, carbonyl, carbonylamino, thioalkyl, sulfonyl, sulfonylamino, acyl, or carboxyl.

In a further aspect of the invention, a compound is provided according to Formula IV

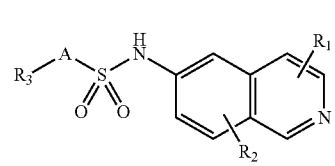

(IV)

wherein A is a substituted or unsubstituted linker consisting of at least one member atom and at most 4 member atoms wherein the linker may be mono- or disubstituted with halogen, cyano, nitro or $C_1$-$C_4$ alkyl, or the substituted atoms may attach back to the main chain to form a ring;

wherein $R_1$, and $R_2$ are, independently, hydrogen, hydroxyl, halogen, $C_1$-$C_4$ alkyl, $C_2$-$C_4$ alkenyl, $C_2$-$C_4$ alkynyl, amino, nitro, cyano, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl or $C_1$-$C_4$ carboxyl; and wherein $R_3$ is hydrogen, halogen, alkyl, alkenyl, alkynyl, alkoxy, amino, cyano, cycloalkyl, heterocycloalkyl, aryl, $C_1$-$C_4$ alkyl aryl, heteroaryl, $C_1$-$C_4$ alkyl heteroaryl, carbonyl, carbonylamino, thioalkyl, sulfonyl, sulfonylamino, acyl, or carboxyl.

In yet a further aspect, a method is provided for influencing the action of a kinase in a cell, a tissue, or a living mammal comprising administering to or contacting with the cell, tissue, or mammal at least one compound according to claim 1, 6, 12 or 16, or increasing the effectiveness of another therapeutic agent in a cell, tissue or living mammal comprising administering to or contacting with the cell, tissue or mammal a therapeutically effective amount of at least one compound according to claim 1, 6, 12 or 16.

In yet another aspect of the invention, a pharmaceutical composition is provided, comprising:

a) a 6-aminoisoquinoline derivative having the structure

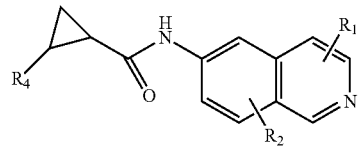

wherein $R_1$, and $R_2$ are, independently, hydrogen, hydroxyl, halogen, $C_1$-$C_4$ alkyl, $C_2$-$C_4$ alkenyl, $C_2$-$C_4$ alkynyl, amino, nitro, cyano; $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl or $C_1$-$C_4$ carboxyl; and wherein $R_4$ is hydrogen, halogen, alkyl, alkenyl, alkynyl, alkoxy, amino, cyano, cycloalkyl, heterocycloalkyl, aryl, $C_1$-$C_4$ alkyl aryl, heteroaryl, $C_1$-$C_4$ alkyl heteroaryl, carbonyl, carbonylamino, thioalkyl, sulfonyl, sulfonylamino, acyl, or carboxyl; and b) a carrier.

In yet a further aspect is provided a method of treating a condition comprising administering to a subject in need of treatment a safe and effective amount of a 6-aminoisoquinoline derivative, wherein the condition is selected from the group consisting of eye disease, bone disorder, obesity, heart disease, hepatic disease, renal disease, pancreatitis, cancer, myocardial infarct, gastric disturbance, hypertension, fertility control, nasal congestion, neurogenic bladder disorder, gastrointestinal disorder, and dermatological disorder.

DETAILED DESCRIPTION

Publications and patents are referred to throughout this disclosure. All U.S. patents cited herein are hereby incorporated by reference. All percentages, ratios, and proportions used herein are percent by weight unless otherwise specified.

Novel 6-aminoisoquinoline compounds and methods of using those compounds to treat disease are provided.

"Alkyl" refers to a saturated aliphatic hydrocarbon including straight chain and branched chain groups. "Alkyl" may be exemplified by groups such as methyl, ethyl, n-propyl, isopropyl, n-butyl and the like. Alkyl groups may be substituted or unsubstituted. Substituents may also be themselves substituted. When substituted, the substituent group is preferably but not limited to $C_1$-$C_4$ alkyl, aryl, amino, cyano, halogen, alkoxy or hydroxyl. "$C_1$-$C_4$ alkyl" refers to alkyl groups containing one to four carbon atoms.

"Alkenyl" refers to an unsaturated aliphatic hydrocarbon moiety including straight chain and branched chain groups. Alkenyl moieties must contain at least one alkene. "Alkenyl" may be exemplified by groups such as ethenyl, n-propenyl, isopropenyl, n-butenyl and the like. Alkenyl groups may be substituted or unsubstituted. Substituents may also be themselves substituted. When substituted, the substituent group is preferably alkyl, halogen or alkoxy. Substitutients may also be themselves substituted. Substituents be placed on the alkene itself and also on the adjacent member atoms or the alkynyl moiety "$C_2$-$C_4$ alkenyl" refers to alkenyl groups containing two to four carbon atoms.

"Alkynyl" refers to an unsaturated aliphatic hydrocarbon moiety including straight chain and branched chain groups. Alkynyl moieties must contain at least one alkyne. "Alkynyl" may be exemplified by groups such as ethynyl, propynyl, n-butynyl and the like. Alkynyl groups may be substituted or unsubstituted. When substituted, the substituent group is preferably alkyl, amino, cyano, halogen, alkoxyl or hydroxyl. Substituents may also be themselves substituted. Substituents are not on the alkyne itself but on the adjacent member atoms of the alkynyl moiety. "$C_2$-$C_4$ alkynyl" refers to alkynyl groups containing two to four carbon atoms.

"Acyl" or "carbonyl" refers to the group —C(O)R wherein R is alkyl; alkenyl; alkyl alkynyl, aryl, heteroaryl, carbocyclic, heterocarbocyclic; $C_1$-$C_4$ alkyl aryl or $C_1$-$C_4$ alkyl heteroaryl. $C_1$-$C_4$ alkylcarbonyl refers to a group wherein the carbonyl moiety is preceded by an alkyl chain of 1-4 carbon atoms.

"Alkoxy" refers to the group —O—R wherein R is acyl, alkyl alkenyl, alkyl alkynyl, aryl, carbocyclic; heterocarbocyclic; heteroaryl, $C_1$-$C_4$ alkyl aryl or $C_1$-$C_4$ alkyl heteroaryl "Amino" refers to the group —NR'R' wherein each R' is, independently, hydrogen, alkyl, aryl, heteroaryl, $C_1$-$C_4$ alkyl aryl or $C_1$-$C_4$ alkyl heteroaryl. The two R' groups may themselves be linked to form a ring.

"Aryl" refers to an aromatic carbocyclic group. "Aryl" may be exemplified by phenyl. The aryl group may be substituted or unsubstituted. Substituents may also be themselves substituted. When substituted, the substituent group is preferably but not limited to heteroaryl; acyl, carboxyl, carbonylamino, nitro, amino, cyano, halogen, or hydroxyl.

"Carboxyl" refers to the group —C(=O)O—$C_1$-$C_4$ alkyl.

"Carbonylamino" refers to the group —C(O)NR'R' wherein each R' is, independently, hydrogen, alkyl, aryl, cycloalkyl; heterocycloalkyl; heteroaryl, $C_1$-$C_4$ alkyl aryl or $C_1$-$C_4$ alkyl heteroaryl. The two R' groups may themselves be linked to form a ring.

"$C_1$-$C_4$ alkyl aryl" refers to $C_1$-$C_4$ alkyl groups having an aryl substituent such that the aryl substituent is bonded through an alkyl group. "$C_1$-$C_4$ alkyl aryl" may be exemplified by benzyl.

"$C_1$-$C_4$ alkyl heteroaryl" refers to $C_1$-$C_4$ alkyl groups having a heteroaryl substituent such that the heteroaryl substituent is bonded through an alkyl group.

"Carbocyclic group" or "cycloalkyl" means a monovalent saturated or unsaturated hydrocarbon ring. Carbocyclic groups are monocyclic, or are fused, spiro, or bridged bicyclic ring systems. Monocyclic carbocyclic groups contain 3 to 10 carbon atoms, preferably 4 to 7 carbon atoms, and more preferably 5 to 6 carbon atoms in the ring. Bicyclic carbocyclic groups contain 8 to 12 carbon atoms, preferably 9 to 10 carbon atoms in the ring. Carbocyclic groups may be substituted or unsubstituted. Substituents may also be themselves substituted. Preferred carbocyclic groups include cyclopropyl, cyclobutyl, cyclopentyl, cyclohexyl, cyclohexenyl, and cycloheptyl. More preferred carbocyclic groups include cyclopropyl and cyclobutyl. The most preferred carbocyclic group is cyclopropyl. Carbocyclic groups are not aromatic.

"Halogen" refers to fluoro, chloro, bromo or iodo moieties. Preferably, the halogen is fluoro, chloro, or bromo.

"Heteroaryl" or "heteroaromatic" refers to a monocyclic or bicyclic aromatic carbocyclic radical having one or more heteroatoms in the carbocyclic ring. Heteroaryl may be substituted or unsubstituted. When substituted, the substituents may themselves be substituted. Preferred but non limiting substituents are aryl; $C_1$-$C_4$ alkylaryl; amino; halogen, hydroxy, cyano, nitro; carboxyl; carbonylamino or $C_1$-$C_4$ alkyl. Preferred heteroaromatic groups include tetrazoyl, triazolyl; thienyl, thiazolyl, purinyl, pyrimidyl, pyridyl, and furanyl. More preferred heteroaromatic groups include benzothiofuranyl; thienyl, furanyl, tetrazoyl, triazolyl; and pyridyl.

"Heteroatom" means an atom other than carbon in the ring of a heterocyclic group or a heteroaromatic group or the chain of a heterogeneous group. Preferably, heteroatoms are selected from the group consisting of nitrogen, sulfur, and oxygen atoms. Groups containing more than one heteroatom may contain different heteroatoms.

"Heterocarbocyclic group" or "heterocycloalkyl" or "heterocyclic" means a monovalent saturated or unsaturated hydrocarbon ring containing at least one heteroatom. Heterocarbocyclic groups are monocyclic, or are fused, spiro, or bridged bicyclic ring systems. Monocyclic heterocarbocyclic groups contain 3 to 10 carbon atoms, preferably 4 to 7 carbon atoms, and more preferably 5 to 6 carbon atoms in the ring.

Bicyclic heterocarbocyclic groups contain 8 to 12 carbon atoms, preferably 9 to 10 carbon atoms in the ring. Heterocarbocyclic groups may be substituted or unsubstituted. Substituents may also be themselves substituted. Preferred heterocarbocyclic groups include epoxy, tetrahydrofuranyl, azacyclopentyl, azacyclohexyl, piperidyl, and homopiperidyl. More preferred heterocarbocyclic groups include piperidyl, and homopiperidyl. The most preferred heterocarbocyclic group is piperidyl. Heterocarbocyclic groups are not aromatic.

"Hydroxy" or "hydroxyl" means a chemical entity that consists of —OH. Alcohols contain hydroxy groups. Hydroxy groups may be free or protected. An alternative name for hydroxyl is hydroxy "Linker" means a linear chain of n member atoms where n is an integer of from 1 to 4.

"Member atom" means a carbon, nitrogen, oxygen or sulfur atom. Member atoms may be substituted up to their normal valence. If substitution is not specified the substituents required for valency are hydrogen.

"Ring" means a collection of member atoms that are cyclic. Rings may be carbocyclic, aromatic, or heterocyclic or heteroaromatic, and may be substituted or unsubstituted, and may be saturated or unsaturated. Ring junctions with the main chain may be fused or spirocyclic. Rings may be monocyclic or bicyclic. Rings contain at least 3 member atoms and at most 10 member atoms. Monocyclic rings may contain 3 to 7 member atoms and bicyclic rings may contain from 8 to 12 member atoms. Bicyclic rings themselves may be fused or spirocyclic.

"Thioalkyl" refers to the group —S-alkyl.

"Sulfonyl" refers to the —S(O)$_2$R' group wherein R' is alkoxy, alkyl, aryl, carbocyclic, heterocarbocyclic; heteroaryl, $C_1$-$C_4$ alkyl aryl or $C_1$-$C_4$ alkyl heteroaryl.

"Sulfonylamino" refers to the —S(O)$_2$NR'R' group wherein each R' is independently alkyl, aryl, heteroaryl, $C_1$-$C_4$ alkyl aryl or $C_1$-$C_4$ alkyl heteroaryl.

"Pharmaceutically acceptable carrier" means a carrier that is useful for the preparation of a pharmaceutical composition that is: generally compatible with the other ingredients of the composition, not deleterious to the recipient, and neither biologically nor otherwise undesirable. "A pharmaceutically acceptable carrier" includes both one and more than one carrier. Embodiments include carriers for topical, ocular, parenteral, intravenous, intraperitoneal intramuscular, sublingual, nasal and oral administration. "Pharmaceutically acceptable carrier" also includes agents for preparation of aqueous dispersions and sterile powders for injection or dispersions.

"Excipient" as used herein includes physiologically compatible additives useful in preparation of a pharmaceutical composition. Examples of pharmaceutically acceptable carriers and excipients can for example be found in Remington Pharmaceutical Science, 16$^{th}$ Ed.

"Therapeutically effective amount" as used herein refers to a dosage of the compounds or compositions effective for influencing, reducing or inhibiting the activity of or preventing activation of a kinase. This term as used herein may also refer to an amount effective at bringing about a desired in vivo effect in an animal, preferably, a human, such as reduction in intraocular pressure.

"Administering" as used herein refers to administration of the compounds as needed to achieve the desired effect.

"Eye disease" as used herein includes, but is not limited to, glaucoma, allergy, cancers of the eye, neurodegenerative diseases of the eye, and dry eye.

The term "disease or condition associated with kinase activity" is used to mean a disease or condition treatable, in whole or in part, by inhibition of one or more kinases.

The term "controlling the disease or condition" is used to mean changing the activity of one or more kinases to affect the disease or condition.

The 6-aminoisoquinoline compounds may be represented by Formula I:

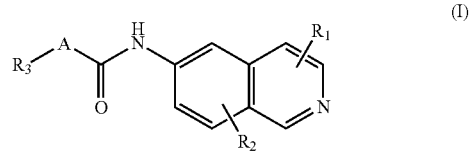

(I)

wherein A is a substituted or unsubstituted linker consisting of at least two member atoms and at most 4 member atoms wherein the linker may be mono- or disubstituted with halogen, cyano, amino, nitro, alkyl, alkenyl or alkynyl, or the substituted atoms may attach back to the main chain to form a ring, wherein $R_3$ is hydrogen; halogen; alkyl; alkenyl; alkynyl; alkoxy; amino; cyano; cycloalkyl; heterocycloalkyl; aryl; $C_1$-$C_4$ alkyl aryl; heteroaryl; $C_1$-$C_4$ alkyl heteroaryl; carbonyl; carbonylamino; thioalkyl; sulfonyl; sulfonylamino; acyl; or carboxyl; and wherein $R_1$, and $R_2$ are, independently, hydrogen; hydroxyl, halogen; $C_1$-$C_4$ alkyl; $C_2$-$C_4$ alkenyl, $C_2$-$C_4$ alkynyl, amino; nitro; cyano; $C_1$-$C_4$ carbonyl; $C_1$-$C_4$ carbonylamino; $C_1$-$C_4$ alkoxy; $C_1$-$C_4$ sulfonyl; $C_1$-$C_4$ sulfonylamino; $C_1$-$C_4$ thioalkyl and $C_1$-$C_4$ carboxyl.

In a preferred embodiment of Formula (I), A is a cyclopropyl ring, $R_3$ is a substituted aromatic ring and $R_1$, $R_2$ are hydrogen. In another preferred embodiment of Formula (I), A is —CH$_2$NH—. In another preferred embodiment of Formula (I), $R_1$, and $R_2$, are hydrogen and $R_3$ is a substituted aromatic ring.

In another embodiment, the 6-aminoisoquinoline compounds may be represented by Formula (II):

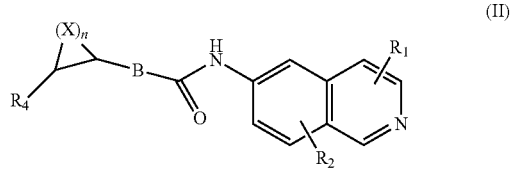

(II)

wherein $R_1$, and $R_2$ are, independently, hydrogen; hydroxyl, halogen; $C_1$-$C_4$ alkyl; $C_2$-$C_4$ alkenyl, $C_2$-$C_4$ alkynyl, amino; nitro; cyano; $C_1$-$C_4$ carbonyl; $C_1$-$C_4$ carbonylamino; $C_1$-$C_4$ alkoxy; $C_1$-$C_4$ sulfonyl; $C_1$-$C_4$ sulfonylamino; $C_1$-$C_4$ thioalkyl and $C_1$-$C_4$ carboxyl. and wherein $R_4$ is hydrogen; halogen; alkyl; alkenyl; alkynyl; alkoxy; amino; cyano; cycloalkyl; heterocycloalkyl; aryl; $C_1$-$C_4$ alkyl aryl; heteroaryl; $C_1$-$C_4$ alkyl heteroaryl; carbonyl; carbonylamino; thioalkyl; sulfonyl; sulfonylamino; acyl; or carboxyl; and B is a chain containing from 0 to 3 member atoms, X represents n independently chosen member atoms which together form a ring structure and n is an integer from about 0 to about 5.

In some preferred embodiments of Formula II, the aminoisoquinolines include those compounds wherein $R_1$ and $R_2$ are hydrogen and B contains 0 (zero) member atoms. In further preferred embodiments, $R_4$ is a meta or para-substituted aromatic ring. In some preferred embodiments $R_4$ is an aromatic ring that is substituted with a halogen in the ortho position and a carbonyl group in the para position.

In another embodiment, the 6-aminoisoquinoline compounds may be represented by Formula (III):

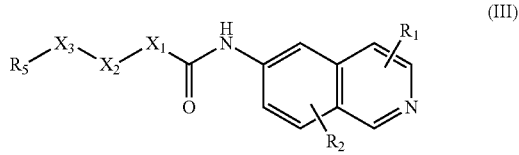
(III)

Wherein one X is independently and uniquely selected from $CH_2$, O, S, S(O), S(O)(O),

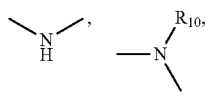

and

The other X groups are chosen from the same list so as to create a stable moiety, or omitted from the formula, wherein $R_1$, and $R_2$ are, independently, hydrogen; hydroxyl, halogen; $C_1$-$C_4$ alkyl; $C_2$-$C_4$ alkenyl, $C_2$-$C_4$ alkynyl, amino; nitro; cyano; $C_1$-$C_4$ carbonyl; $C_1$-$C_4$ carbonylamino; $C_1$-$C_4$ alkoxy; $C_1$-$C_4$ sulfonyl; $C_1$-$C_4$ sulfonylamino; $C_1$-$C_4$ thioalkyl and $C_1$-$C_4$ carboxyl; and $R_5$ and $R_{10}$ are independently hydrogen; halogen; alkyl; alkenyl; alkynyl; alkoxy; amino; cyano; cycloalkyl; heterocycloalkyl; aryl; $C_1$-$C_4$ alkyl aryl; heteroaryl; $C_1$-$C_4$ alkyl heteroaryl; carbonyl; carbonylamino; thioalkyl; sulfonyl; sulfonylamino; acyl; or carboxyl; and A 6-aminoisoquinoline compound according to Formula IV is further provided:

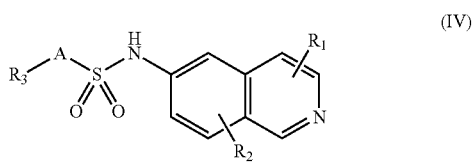
(IV)

wherein A is a substituted or unsubstituted linker consisting of at least one member atom and at most 4 member atoms wherein the linker may be mono- or disubstituted with halogen, cyano, nitro or $C_1$-$C_4$ alkyl, or the substituted atoms may attach back to the main chain to form a ring, and wherein $R_3$ is hydrogen; halogen; alkyl; alkenyl; alkynyl; alkoxy; amino; cyano; cycloalkyl; heterocycloalkyl; aryl; $C_1$-$C_4$ alkyl aryl; heteroaryl; $C_1$-$C_4$ alkyl heteroaryl; carbonyl; carbonylamino; thioalkyl; sulfonyl; sulfonylamino; acyl; or carboxyl; and wherein $R_1$, and $R_2$ are, independently, hydrogen; hydroxyl, halogen; $C_1$-$C_4$ alkyl; $C_2$-$C_4$ alkenyl, $C_2$-$C_4$ alkynyl, amino; nitro; cyano; $C_1$-$C_4$ carbonyl; $C_1$-$C_4$ carbonylamino; $C_1$-$C_4$ alkoxy; $C_1$-$C_4$ sulfonyl; $C_1$-$C_4$ sulfonylamino; $C_1$-$C_4$ thioalkyl and $C_1$-$C_4$ carboxyl.

In some preferred embodiments of Formula IV, the aminoisoquinolines include those compounds wherein $R_1$ and $R_2$ are hydrogen and A is ethyl or ethenyl. In further preferred embodiments, $R_3$ is a meta or para-substituted aromatic ring. In some preferred embodiments $R_3$ is an aromatic ring that is substituted with a halogen in the ortho position and a carbonyl group in the para position. In some preferred embodiments A is —O—$CH_2$— or —NH—$CH_2$—.

The carbon linked 6-aminoisoquinoline compounds may be synthesized by the general scheme set forth below:

Scheme One

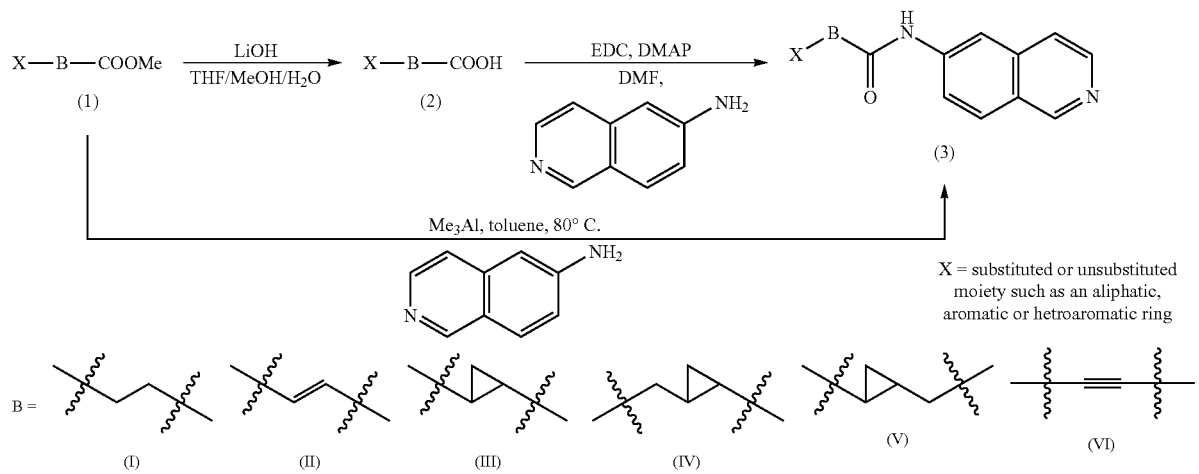

Scheme One: The selected aromatic ester (1) was saponified with an appropriate base such as LiOH to form the free acid (2) then coupled to 6-aminoisoquinoline using standard coupling procedures such as EDC and DMAP in DMF to form the desired compound (3). Alternatively, the ester (1) was reacted with the trimethyl aluminum amide of 6-aminoisoquinoline to generate the amide (3) directly.

Intermediates (1) of the type III and IV from Scheme One may be synthesized by the general scheme, Scheme Two set forth below:

Scheme Two

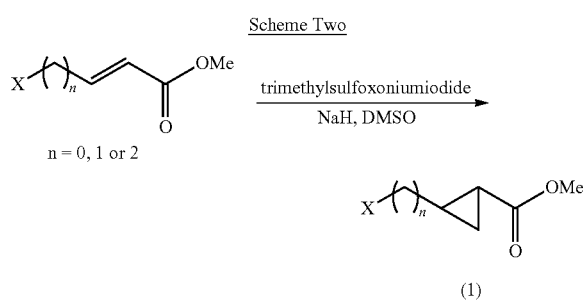

Scheme Two: The selected ester is reacted with trimethylsulfoxonium ylide to give the desired cyclopropyl intermediate (1) for use in Scheme One.

When intermediates (1) of the type III or IV are aromatic rings substituted in the meta or para positions with amides or esters, they are synthesized by the general scheme set forth below:

Scheme Three

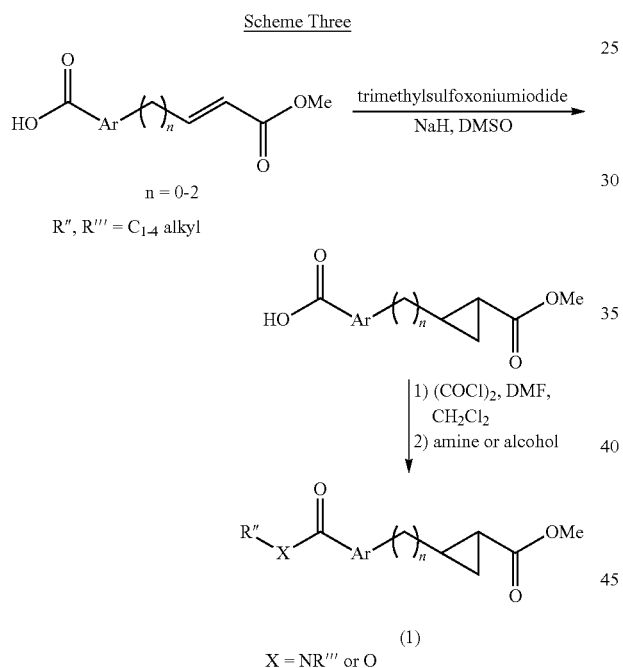

Scheme Three: The selected allylic ester was converted to a cyclopropane with trimethyl sulfoxonium ylide. The aromatic acid group of the formed cyclopropane was then converted to its acid chloride using standard procedures then reacted with the appropriate alcohol or amine to give the desired intermediate (1).

Scheme Four

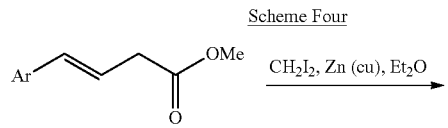

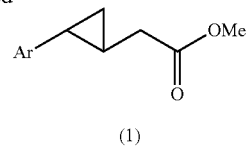

Scheme Four: The appropriate ester is converted to a cyclopropane under Simmons-Smith conditions to give the desired intermediate (1).

Using Scheme Five, compounds of Formula III with substituted 6-amino isoquinolines (1) are prepared.

Scheme Five

Scheme 5

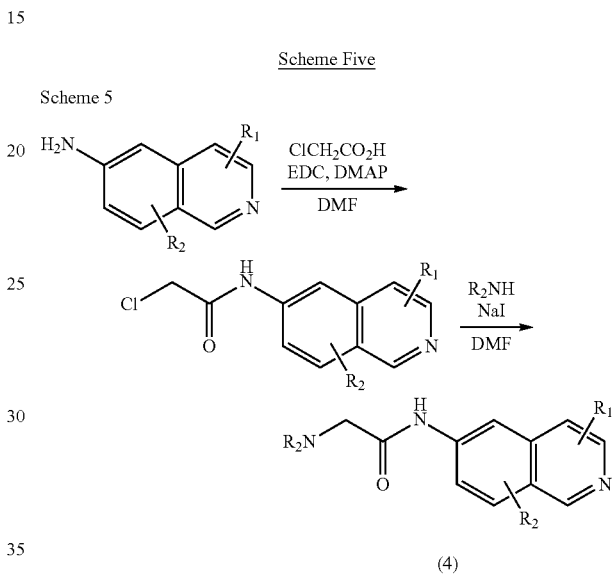

Scheme Five: Chloroacetic acid is treated with EDC in the presence of DMAP and then the substituted 6-aminoisoquinoline. The resulting amide is treated with sodium iodide and an amine to provide the final product amine 4.

Using Scheme Six, the compound with a sulfonamide group according to Formula IV may be prepared.

Scheme Six

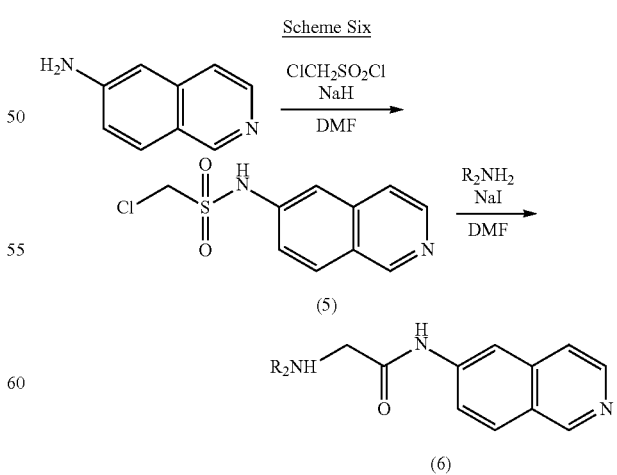

Scheme Six: 6-Aminoisoquinoline is treated with sodium hydride and then chloromethanesulfonyl chloride to provide the sulfonamide 5. Treatment of the chlorosulfonamide 5 with an amine in the presence of sodium iodide provides the desired amine 6.

Using reactions similar to those in Scheme Five, compounds with a cycloalkyl moiety can be prepared. The compounds are obtained by using a cycloalkylamine instead of an aniline to displace the chloride (Scheme Seven).

Scheme Seven

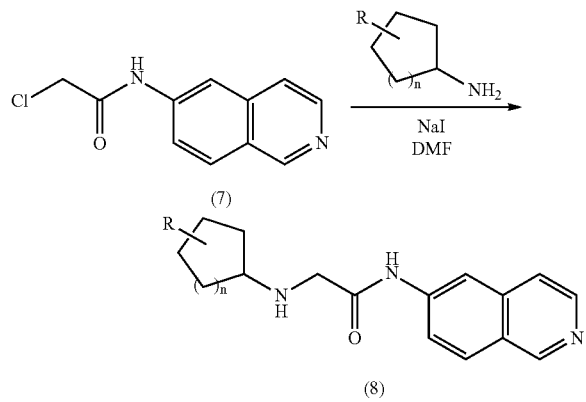

(7)

(8)

Scheme Seven: Treatment of the chloroamide 7 with an amine in the presence of sodium iodide provides the desired product 8.

The abbreviations used in the synthetic schemes shown have the following meanings: $Boc_2O$ means di-tert-butyl-dicarbonate, DMAP means dimethyl aminopyridine, DMSO means Dimethyl Sulfoxide, HATU means 2-(7-Aza-1H-benzotriazole-1-yl)-1,1,3,3-tetramethyluronium hexafluorophosphate, LDA means lithium diisopropyl amide, DMF is dimethylformamide, THF is tetrahydrofuran, and EDC means N-(3-dimethylaminopropyl)-N'-ethylcarbodiimide hydrochloride.

The 6-aminoisoquinoline compounds of the above Formulae and compositions including them have kinase inhibitory activity and are thus useful in influencing or inhibiting the action of kinases, and in treatment and/or prevention of diseases or conditions influenced by kinases. The 6-aminoisoquinolines may be used to influence or inhibit the action of kinases either in a cell in vitro or in a cell in a living body in vivo. Specifically, in one embodiment, a method is provided of inhibiting the action of a kinase comprising applying to a medium such as an assay medium or contacting with a cell either in a cell in vitro or in a cell in a living body in vivo an effective inhibitory amount of a compound according to Formula (I) or (II) or (III) or (IV). In a preferred embodiment, the kinase inhibited is a rho kinase. Compounds according to Formula (I) or (II) or (III) or (IV) are used in methods of inhibiting kinases in a cell, a tissue or an animal such as a human comprising administering to, or contacting with, the cell a therapeutically effective amount of one or more of these 6-aminoisoquinolines. The one or more of the 6-aminoisoquinolines are preferably administered in a pharmaceutically acceptable formulation, such as in or with a pharmaceutically acceptable carrier when the 6-aminoisoquinolines are administered to a cell or cells in a living organism or body. In another embodiment, the 6-aminoisoquinolines according to Formula (I) or (II) or (III) or (IV) are used in methods for influencing the action of a kinase in a cell comprising administering to, or contacting with, the cell an effective amount of one or more 6-aminoisoquinolines for influencing the action of the kinase in the cell. The one or more of the 6-aminoisoquinolines are preferably administered in a pharmaceutically acceptable formulation, such as in or with a pharmaceutically acceptable carrier when the 6-aminoisoquinolines are administered to a cell or cells in a living organism or body.

Treatment or prevention of diseases or conditions for which the 6-aminoisoquinolines may be useful includes any of the diseases or conditions associated with kinase activity or diseases or conditions affected by kinases. Examples of these types of diseases include retinal degradation, glaucoma and cancer.

The 6-aminoisoquinolines in some embodiments will be administered in conjunction with the administration of a second or in some cases a third therapeutic agent which is directed to the treatment or prevention of a condition or disease affected by those specific receptors. Combining administration of the 6-aminoisoquinolines with other therapeutic agents will provide a reduction or prevention of the condition or disease to which the therapeutic agent is directed, resulting in improving the ability of the therapeutic agent to have the desired effect over a longer period of time. Additionally, the administration of the therapeutic agent or receptor agonist with an 6-aminoisoquinoline formulation will enable lower doses of the other therapeutic agents to be administered for a longer period of time.

One or more therapeutic agents may be administered with one or more 6-aminoisoquinoline compounds. The therapeutic agents and/or the 6-aminoisoquinoline compounds are preferably administered in a pharmaceutically acceptable formulation with a pharmaceutically acceptable carrier when the 6-aminoisoquinolines are administered to a cell or cells in a living organism or a mammal, preferably human.

Compositions including the 6-aminoisoquinolines of Formula (I) or (II) or (III) or (IV) may be obtained in the form of various salts or solvates. As the salts, physiologically acceptable salts or salts available as raw materials are used.

Compositions may include one or more of the isoforms of Formula (I) or (II) or (III) or (IV) when present. When a stereocenter exists, each enantiomer may be separately used, or they may be combined in any proportion.

Pharmaceutical compositions for use in accordance with the present invention may be formulated in a conventional manner using one or more physiologically acceptable carriers or excipients. Thus, the compounds and their physiologically acceptable salts and solvates may be formulated for administration by, for example, solid dosing, eyedrop, in a topical oil-based formulation, injection, inhalation (either through the mouth or the nose), oral, buccal, parenteral or rectal administration. Techniques and formulations may generally be found in "Remington's Pharmaceutical Sciences", (Meade Publishing Co., Easton, Pa.). Therapeutic compositions must typically be sterile and stable under the conditions of manufacture and storage.

Compositions of the present invention may comprise a safe and effective amount of the subject compounds, and a pharmaceutically-acceptable carrier. As used herein, "safe and effective amount" means an amount of a compound sufficient to significantly induce a positive modification in the condition to be treated, but low enough to avoid serious side effects (at a reasonable benefit/risk ratio), within the scope of sound medical judgment. A safe and effective amount of a compound will vary with the particular condition being treated, the age and physical condition of the patient being treated, the severity of the condition, the duration of the treatment, the nature of concurrent therapy, the particular pharmaceutically-acceptable carrier utilized, and like factors within the knowledge and expertise of the attending physician.

The route by which the A compound of the present invention (component A) will be administered and the form of the composition will dictate the type of carrier (component B) to be used. The composition may be in a variety of forms, suitable, for example, for systemic administration (e.g., oral, rectal, nasal, sublingual, buccal, or parenteral) or topical administration (e.g., local application on the skin, ocular, liposome delivery systems, or iontophoresis).

Carriers for systemic administration typically comprise at least one of a) diluents, b) lubricants, c) binders, d) disintegrants, e) colorants, f) flavors, g) sweeteners, h) antioxidants, j) preservatives, k) glidants, m) solvents, n) suspending agents, o) wetting agents, p) surfactants, combinations thereof, and others. All carriers are optional in the systemic compositions.

Ingredient a) is a diluent. Suitable diluents for solid dosage forms include sugars such as glucose, lactose, dextrose, and sucrose; diols such as propylene glycol; calcium carbonate; sodium carbonate; sugar alcohols, such as glycerin; mannitol; and sorbitol. The amount of ingredient a) in the systemic or topical composition is typically about 50 to about 90%.

Ingredient b) is a lubricant. Suitable lubricants for solid dosage forms are exemplified by solid lubricants including silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of *theobroma*. The amount of ingredient b) in the systemic or topical composition is typically about 5 to about 10%.

Ingredient c) is a binder. Suitable binders for solid dosage forms include polyvinylpyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of ingredient c) in the systemic composition is typically about 5 to about 50%, and in ocular solid dosing forms up to 99%.

Ingredient d) is a disintegrant. Suitable disintegrants for solid dosage forms include agar, alginic acid and the sodium salt thereof, effervescent mixtures, croscarmelose, crospovidone, sodium carboxymethyl starch, sodium starch glycolate, clays, and ion exchange resins. The amount of ingredient d) in the systemic or topical composition is typically about 0.1 to about 10%.

Ingredient e) for solid dosage forms is a colorant such as an FD&C dye. When used, the amount of ingredient e) in the systemic or topical composition is typically about 0.005 to about 0.1%.

Ingredient f) for solid dosage forms is a flavor such as menthol, peppermint, and fruit flavors. The amount of ingredient f), when used, in the systemic or topical composition is typically about 0.1 to about 1.0%.

Ingredient g) for solid dosage forms is a sweetener such as aspartame and saccharin. The amount of ingredient g) in the systemic or topical composition is typically about 0.001 to about 1%.

Ingredient h) is an antioxidant such as butylated hydroxyanisole ("BHA"), butylated hydroxytoluene ("BHT"), and vitamin E. The amount of ingredient h) in the systemic or topical composition is typically about 0.1 to about 5%.

Ingredient j) is a preservative such as benzalkonium chloride, methyl paraben and sodium benzoate. The amount of ingredient j) in the systemic or topical composition is typically about 0.01 to about 5%.

Ingredient k) for solid dosage forms is a glidant such as silicon dioxide. The amount of ingredient k) in the systemic or topical composition is typically about 1 to about 5%.

Ingredient m) is a solvent, such as water, isotonic saline, ethyl oleate, glycerine, hydroxylated castor oils, alcohols such as ethanol, and phosphate buffer solutions. The amount of ingredient m) in the systemic or topical composition is typically from about 0 to about 100%.

Ingredient n) is a suspending agent. Suitable suspending agents include AVICEL® RC-591 (from FMC Corporation of Philadelphia, Pa.) and sodium alginate. The amount of ingredient n) in the systemic or topical composition is typically about 1 to about 8%.

Ingredient o) is a surfactant such as lecithin, polysorbate 80, and sodium lauryl sulfate, and the TWEENS® from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of ingredient o) in the systemic or topical composition is typically about 0.1% to about 5%.

Although the amounts of components A and B in the systemic compositions will vary depending on the type of systemic composition prepared, the specific derivative selected for component A and the ingredients of component B, in general, system compositions comprise 0.01% to 50% of component A and 50 to 99.99% of component B.

Compositions for parenteral administration typically comprise A) 0.1 to 10% of the compounds of the present invention and B) 90 to 99.9% of a carrier comprising a) a diluent and m) a solvent. In one embodiment, component a) comprises propylene glycol and m) comprises ethanol or ethyl oleate.

Compositions for oral administration can have various dosage forms. For example, solid forms include tablets, capsules, granules, and bulk powders. These oral dosage forms comprise a safe and effective amount, usually at least about 5%, and more particularly from about 25% to about 50% of component A). The oral dosage compositions further comprise about 50 to about 95% of component B), and more particularly, from about 50 to about 75%.

Tablets can be compressed, tablet triturates, enteric-coated, sugar-coated, film-coated, or multiple-compressed. Tablets typically comprise component A, and component B a carrier comprising ingredients selected from the group consisting of a) diluents, b) lubricants, c) binders, d) disintegrants, e) colorants, f) flavors, g) sweeteners, k) glidants, and combinations thereof. Specific diluents include calcium carbonate, sodium carbonate, mannitol, lactose and cellulose. Specific binders include starch, gelatin, and sucrose. Specific disintegrants include alginic acid and croscarmelose. Specific lubricants include magnesium stearate, stearic acid, and talc. Specific colorants are the FD&C dyes, which can be added for appearance. Chewable tablets preferably contain g) sweeteners such as aspartame and saccharin, or f) flavors such as menthol, peppermint, fruit flavors, or a combination thereof.

Capsules (including time release and sustained release formulations) typically comprise component A, and a carrier comprising one or more a) diluents disclosed above in a capsule comprising gelatin. Granules typically comprise component A, and preferably further comprise k) glidants such as silicon dioxide to improve flow characteristics.

The selection of ingredients in the carrier for oral compositions depends on secondary considerations like taste, cost, and shelf stability, which are not critical for the purposes of this invention. One skilled in the art would know how to select appropriate ingredients without undue experimentation.

The solid compositions may also be coated by conventional methods, typically with pH or time-dependent coatings, such that component A is released in the gastrointestinal tract in the vicinity of the desired application, or at various points and times to extend the desired action. The coatings typically comprise one or more components selected from the group consisting of cellulose acetate phthalate, polyvinyl acetate phthalate, hydroxypropyl methyl cellulose phthalate, ethyl cellulose, EUDRAGIT® coatings (available from Rohm & Haas G.M.B.H. of Darmstadt, Germany), waxes and shellac.

Compositions for oral administration can also have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically comprise component A and component B, namely, a carrier comprising ingredients selected from the group consisting of a) diluents, e) colorants, f) flavors, g) sweeteners, j) preservatives, m) solvents, n) suspending agents, and o) surfactants. Peroral liquid compositions preferably comprise one or more ingredients selected from the group consisting of e) colorants, f) flavors, and g) sweeteners.

Other compositions useful for attaining systemic delivery of the subject compounds include sublingual, buccal and nasal dosage forms. Such compositions typically comprise one or more of soluble filler substances such as a) diluents including sucrose, sorbitol and mannitol; and c) binders such as *acacia*, microcrystalline cellulose, carboxymethyl cellulose, and hydroxypropyl methylcellulose. Such compositions may further comprise b) lubricants, e) colorants, f) flavors, g) sweeteners, h) antioxidants, and k) glidants.

In one embodiment of the invention, the compounds of the present invention are topically administered. Topical compositions that can be applied locally to the eye may be in any form known in the art, non-limiting examples of which include solids, gelable drops, sprays, ointments, or a sustained or non-sustained release unit placed in the conjunctival cul-du-sac of the eye or another appropriate location.

Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions comprise: component A, the compounds described above, and component B, a carrier. The carrier of the topical composition preferably aids penetration of the compounds into the eye. Component B may further comprise one or more optional components.

The dosage range of the compound for systemic administration is from about 0.01 to about 1000 µg/kg body weight, preferably from about 0.1 to about 100 µg/kg per body weight, most preferably form about 1 to about 50 µg/kg body weight per day. The transdermal dosages will be designed to attain similar serum or plasma levels, based upon techniques known to those skilled in the art of pharmacokinetics and transdermal formulations. Plasma levels for systemic administration are expected to be in the range of 0.01 to 100 nanograms/mL, (ng/mL) more preferably from 0.05 to 50 ng/mL and most preferably from 0.1 to 10 ng/mL. While these dosages are based upon a daily administration rate, weekly or monthly accumulated dosages may also be used to calculate the clinical requirements.

Dosages may be varied based on the patient being treated, the condition being treated, the severity of the condition being treated, the route of administration, etc. to achieve the desired effect.

The compounds of the present invention are useful in decreasing intraocular pressure. Thus, these compounds are useful in the treatment of glaucoma. The preferred route of administration for treating glaucoma is topically.

The exact amounts of each component in the topical composition depend on various factors. The amount of component A added to the topical composition is dependent on the $IC_{50}$ of component A, typically expressed in nanomolar (nM) units. For example, if the $IC_{50}$ of the medicament is 1 nM, the amount of component A will be from about 0.0001 to about 0.1%. If the $IC_{50}$ of the medicament is 10 nM, the amount of component A) will be from about 0.01 to about 1%. If the $IC_{50}$ of the medicament is 100 nM, the amount of component A will be from about 0.1 to about 10%. If the $IC_{50}$ of the medicament is 1000 nM, the amount of component A will be 1 to 100%, preferably 5% to 50%. If the amount of component A is outside the ranges specified above (i.e., lower), efficacy of the treatment may be reduced. One skilled in the art would know how to calculate an $IC_{50}$. The remainder of the composition, up to 100%, is component B.

The amount of the carrier employed in conjunction with component A is sufficient to provide a practical quantity of composition for administration per unit dose of the medicament. Techniques and compositions for making dosage forms useful in the methods of this invention are described in the following references: *Modern Pharmaceutics*, Chapters 9 and 10, Banker & Rhodes, eds. (1979); Lieberman et al., *Pharmaceutical Dosage Forms: Tablets* (1981); and Ansel, *Introduction to Pharmaceutical Dosage Forms*, $2^{nd}$ Ed., (1976).

Component B may comprise a single ingredient or a combination of two or more ingredients. In the topical compositions, component B comprises a topical carrier. Suitable topical carriers comprise one or more ingredients selected from the group consisting of phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols and symmetrical alcohols.

The carrier of the topical composition may further comprise one or more ingredients selected from the group consisting of q) emollients, r) propellants, s) solvents, t) humectants, u) thickeners, v) powders, w) fragrances, x) pigments, and y) preservatives.

Ingredient q) is an emollient. The amount of ingredient q) in a skin-based topical composition is typically about 5 to about 95%. Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, *arachis* oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane.

Ingredient r) is a propellant. The amount of ingredient r) in the topical composition is typically about 0 to about 95%. Suitable propellants include propane, butane, isobutane, dimethyl ether, carbon dioxide, nitrous oxide, and combinations thereof.

Ingredient s) is a solvent. The amount of ingredient s) in the topical composition is typically about 0 to about 95%. Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols.

Ingredient t) is a humectant. The amount of ingredient t) in the topical composition is typically 0 to 95%. Suitable humectants include glycerin, sorbitol, sodium 2-pyrrolidone-5-carboxylate, soluble collagen, dibutyl phthalate, gelatin, and combinations thereof. Specific humectants include glycerin.

Ingredient u) is a thickener. The amount of ingredient u) in the topical composition is typically about 0 to about 95%.

Ingredient v) is a powder. The amount of ingredient v) in the topical composition is typically 0 to 95%. Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified montmorillonite clay, hydrated aluminum silicate, fumed silica, carboxyvinyl polymer, sodium carboxymethyl cellulose, ethylene glycol monostearate, and combinations thereof. For ocular applications, specific powders include beta-cyclodextrin, hydroxypropyl cyclodextrin, and sodium polyacrylate. For gel dosing ocular formulations, sodium polyacrylate may be used.

Ingredient w) is a fragrance. The amount of ingredient w) in the topical composition is typically about 0 to about 0.5%, particularly, about 0.001 to about 0.1%. For ocular applications a fragrance is not typically used.

Ingredient x) is a pigment. Suitable pigments for skin applications include inorganic pigments, organic lake pigments, pearlescent pigments, and mixtures thereof. Inorganic pigments useful in this invention include those selected from the group consisting of rutile or anatase titanium dioxide, coded in the Color Index under the reference CI 77,891; black, yellow, red and brown iron oxides, coded under references CI 77,499, 77,492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

The organic pigments and lakes useful in this invention include those selected from the group consisting of D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430), the dye or lakes based on Cochineal Carmine (CI 75,570) and mixtures thereof.

The pearlescent pigments useful in this invention include those selected from the group consisting of the white pearlescent pigments such as mica coated with titanium oxide, bismuth oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof. The amount of pigment in the topical composition is typically about 0 to about 10%. For ocular applications a pigment is generally not used.

In a particularly preferred embodiment of the invention, topical pharmaceutical compositions for ocular administration are prepared typically comprising component A and B (a carrier), such as purified water, and one or more ingredients selected from the group consisting of y) sugars or sugar alcohols such as dextrans, particularly mannitol and dextran 70, z) cellulose or a derivative thereof, aa) a salt, bb) disodium EDTA (Edetate disodium), and cc) a pH adjusting additive.

Examples of z) cellulose derivatives suitable for use in the topical pharmaceutical composition for ocular administration include sodium carboxymethylcellulose, ethylcellulose, methylcellulose, and hydroxypropyl-methylcellulose, particularly, hydroxypropyl-methylcellulose.

Examples of aa) salts suitable for use in the topical pharmaceutical composition for ocular administration include mono-, di- and trisodium phosphate, sodium chloride, potassium chloride, and combinations thereof.

Examples of cc) pH adjusting additives include HCl or NaOH in amounts sufficient to adjust the pH of the topical pharmaceutical composition for ocular administration to 5.8-7.5.

Component A may be included in kits comprising component A, a systemic or topical composition described above, or both; and information, instructions, or both that use of the kit will provide treatment for cosmetic and medical conditions in mammals (particularly humans). The information and instructions may be in the form of words, pictures, or both, and the like. In addition or in the alternative, the kit may comprise the medicament, a composition, or both; and information, instructions, or both, regarding methods of application of medicament, or of composition, preferably with the benefit of treating or preventing cosmetic and medical conditions in mammals (e.g., humans).

The invention will be further explained by the following illustrative examples that are intended to be non-limiting.

Procedures for preparation of the 6-aminoisoquinolines are described in the following examples.

All temperatures are given in degrees Centigrade. Reagents and starting materials were purchased from commercial sources or prepared following published literature procedures.

Unless otherwise noted, HPLC purification, when appropriate, was performed by redissolving the compound in a small volume of DMSO and filtering through a 0.45 micron (nylon disc) syringe filter. The solution was then purified using, for example, a 50 mm Varian Dynamax HPLC 21.4 mm Micros orb Guard-8 $C_8$ column. A typical initial eluting mixture of 40-80% MeOH:$H_2O$ was selected as appropriate for the target compound. This initial gradient was maintained for 0.5 minutes then increased to 100% MeOH:0% $H_2O$ over 5 minutes. 100% MeOH was maintained for 2 more minutes before re-equilibration back to the initial starting gradient. A typical total run time was 8 minutes. The resulting fractions were analyzed, combined as appropriate, and then evaporated to provide purified material.

Proton magnetic resonance ($^1$H NMR) spectra were recorded on either a Varian NOVA 400 MHz ($^1$H) NMR spectrometer, Varian INOVA 500 MHz ($^1$H) NMR spectrometer, Bruker ARX 300 MHz ($^1$H) NMR spectrometer, Bruker DPX 400 MHz ($^1$H) NMR spectrometer, or a Bruker DRX 500 MHz ($^1$H) NMR spectrometer. All spectra were determined in the solvents indicated. Although chemical shifts are reported in ppm downfield of tetramethylsilane, they are referenced to the residual proton peak of the respective solvent peak for $^1$H NMR. Interproton coupling constants are reported in Hertz (Hz). Analytical HPLC was performed using a Phenomenex Aqua 5 micron $C_{18}$ 125 Å 50×4.60 mm column coupled with an Agilent 1100 series VWD UV detector. A neutral 0.1% BES (w/v) pH 7.1 buffer with LiOH and 1% $CH_3CN$ in $H_2O$ is used as the aqueous phase. The initial gradient was 55% MeOH aqueous buffer which was increased to 100% MeOH over 3 minutes. 100% MeOH was maintained for 2 minutes before it was re-equilibrated to the initial starting gradient. Spectra were analyzed at 254 nm. LCMS spectra were obtained using a Thermofinnigan AQA MS ESI instrument. The samples were passed through a Phenomenex Aqua 5 micron $C_{18}$ 125 Å 50×4.60 mm column. The initial gradient was 55% MeOH: 1% $CH_3CN$ in $H_2O$ which was increased to 100% MeOH over 3 minutes. 100% MeOH was maintained for 2 minutes before it was re-equilibrated to the initial starting gradient. The spray setting for the MS probe was at 350 µL/min with a cone voltage at 25 mV and a probe temperature at 450° C.

The following preparations illustrate procedures for the preparation of intermediates and methods for the preparation of 6-aminoisoquinolines.

EXAMPLE 1

Preparation of 2-chloro-N-(isoquinolin-6-yl) acetamide (E1)

To chloroacetic acid in DMF was added EDC, DMAP and 6-aminoisoquinoline. This mixture was stirred for 4 hours. The reaction was washed with $NaHCO_3$(sat), extracted with EtOAc, dried ($Na_2SO_4$), filtered and evaporated. Column chromatography ($SiO_2$, 5% MeOH/$CH_2Cl_2$) gave 2-chloro-N-(isoquinolin-6-yl)acetamide (E1).

EXAMPLE 2

Preparation of N-(isoquinolin-6-yl)-3-phenylpropanamide (E2)

To 6-aminoisoquinoline in DMF cooled to 0° C. was added NaH and the solution was stirred for 30 minutes at 0° C. Then hydrocinnamoyl chloride was added and the mixture was stirred for 4 hours at room temperature. The mixture was diluted with EtOAc, extracted with $NaHCO_3$(sat), dried ($Na_2SO_4$), filtered and evaporated. Column chromatography ($SiO_2$, 10% hexanes/EtOAc) gave N-(isoquilin-6-yl)-3-phenylpropanamide (E2).

Using largely the procedures set forth in Examples 1-2 and substituting the appropriate starting materials, the compounds 3-7 were made.

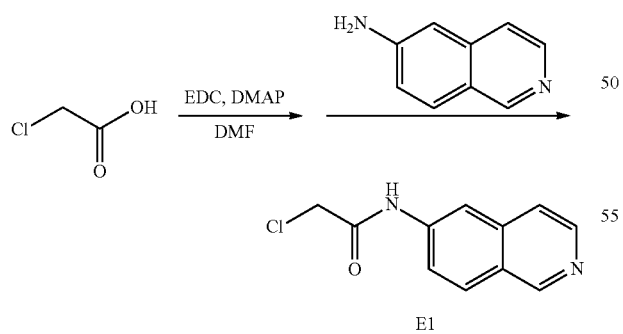

| Example No. | R |
|---|---|
| 3 | $CH_3$ |
| 4 | m-$CH_2$—$C_6H_4$—OMe |
| 5 | |
| 6 | |
| 7 | trans-CH=CH—$C_6H_5$ |

Similarly, using largely the procedures set forth in Examples 1-2 and substituting the appropriate starting materials, the compounds 8-38 can be made.

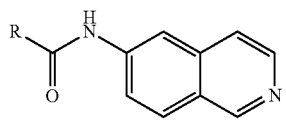

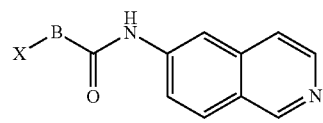

| Example No. | R |
|---|---|
| 8, 9, 10, 11, 12 | $CH_2CH_3$, $CH_2CH_2CH_3$, $CH_2CH=CH_2$, $CH(CH_3)_2$, $C(CH_3)_3$ |
| 13, 14, 15 | $CH_2F$, $CHF_2$, $CF_3$ |
| 16, 17, 18, 19, 20, 21 | $CH_2OH$, $CH_2OMe$, $CH_2OEt$, $CH_2OBn$, $CH_2OAc$, $CH_2OBz$ |
| 22, 23, 24, 25, 26, 27, 28, 29, 30 |  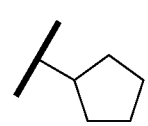  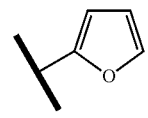 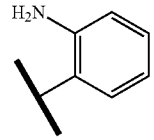 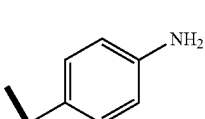 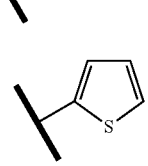 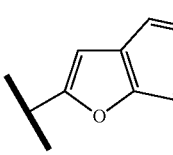 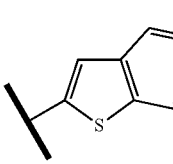 |

| Example No. | B | X |
|---|---|---|
| 31 | $CH_2$ | m-$C_6H_4$—Cl |
| 32 | $CH_2$ | p-$C_6H_4$—F |
| 33 | $CH_2$—$CH_2$ | m-$C_6H_4$—$CO_2Me$ |
| 34 | $CH_2$—$CH_2$ | m-$C_6H_4$—$CONH_2$ |
| 35 | $CH_2$—$CH_2$ | m-$C_6H_4$—CONHMe |
| 36 | CH=CH | m-$C_6H_4$—$CO_2Me$ |
| 37 | $CH_2CH_2$ | m-$C_6H_4$—CONHBn |
| 38 | CH=CH | o-$C_6H_4$—Cl |

EXAMPLE 39

Preparation of tert-butyl 2-(isoquinolin-6-ylamino)-2-oxoethyl carbamate (E39)

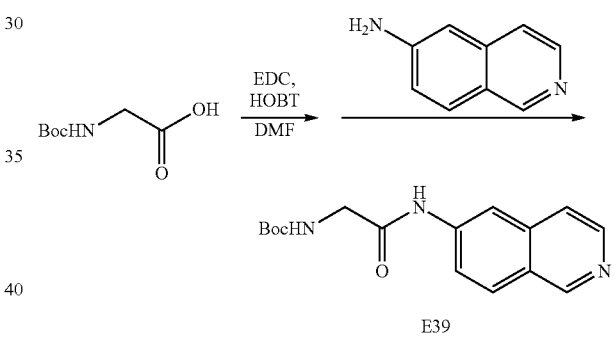

To N-Boc-glycine in DMF was added EDC, HOBT and 6-aminoisoquinoline. This mixture was stirred for 8 hours. The reaction was washed with $NaHCO_3$(sat), extracted with EtOAc, dried ($Na_2SO_4$), filtered and evaporated. Column chromatography ($SiO_2$, MeOH/$CH_2Cl_2$) gave tert-butyl 2-(isoquinolin-6-ylamino)-2-oxoethyl carbamate (E39).

EXAMPLE 40

Preparation of 2-amino-N-isoquinoline-6-yl-acetamide hydrochloride (E40)

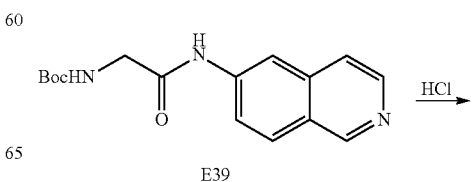

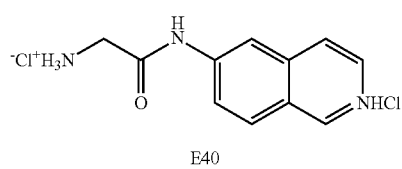

E40

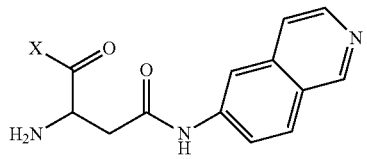

| Example No. | X |
|---|---|
| 53 | OH |
| 54 | OMe |
| 55 | NHMe |
| 56 | $NHC_6H_5$ |
| 57 | $m\text{-}NHC_6H_4\text{—}OMe$ |

EXAMPLE 58

Preparation of 2-(benzylamino)-N-(isoquinolin-6-yl) acetamide (E58)

To tert-butyl 2-(isoquinolin-6-ylamino)-2-oxoethyl carbamate (E39) in $CH_2Cl_2$ was added HCl (4M) in dioxane and the solution was stirred overnight at room temperature. The reaction was concentrated to give 2-amino-N-isoquinoline-6-yl-acetamide dihydrochloride (E40).

Using largely the procedures set forth in Examples 39-40 and substituting the appropriate starting materials, the compounds 41-57 can be made.

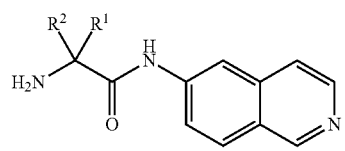

| Example No. | $R^1$ | $R^2$ | $R^1$-$R^2$ (together form a ring) |
|---|---|---|---|
| 41 | H | Me | — |
| 42 | H | $CH_2C_6H_5$ | — |
| 43 | H | $p\text{-}CH_2C_6H_4OH$ | — |
| 44 | H | $p\text{-}CH_2C_6H_4OMe$ | — |
| 45 | H | $CH_2CO_2Me$ | — |
| 46 | H | $CH_2CH_2CO_2Me$ | — |
| 47 | H | $CH_2CONH_2$ | — |
| 48 | H | $CH_2CH_2CONH_2$ | — |
| 49 | Me | Me | — |
| 50, 51, 52 | — | — | △, ⬠, ⬡ |

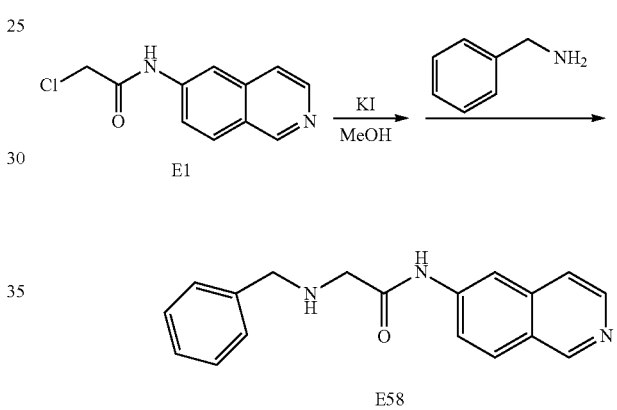

To 2-chloro-N-(isoquinolin-6-yl)acetamide (E1) in MeOH was added KI and the solution was heated to 60° C. for 40 minutes. The mixture was cooled to 45° C. and benzylamine was added and stirred at 45° C. After 2-4 hours, the solvents were evaporated and the residue was taken up in EtOAc and extracted with $NaHCO_3$(sat). The organics were dried ($Na_2SO_4$), filtered and evaporated. Flash chromatography ($SiO_2$, 2% $NH_3$(2M) in MeOH/3% MeOH/$CH_2Cl_2$) gave purified 2-(benzylamino)-N-(isoquinolin-6-yl)acetamide (E58).

EXAMPLE 59

Example of N-(isoquinolin-6-yl)-2-(3-methoxybenzylamino)acetamide (E59)

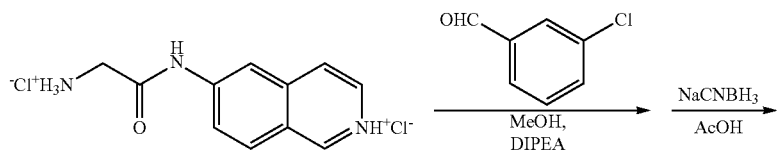

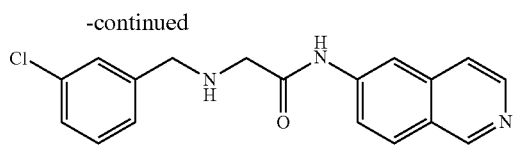

E59

To m-chlorobenzaldehyde in MeOH was added 2-amino-N-(isoquinolin-6-yl)acetamide dihydrochloride (from Example 40) and the pH was adjusted to 5 with DIPEA. The mixture was stirred at room temperature for 2 hours, then NaCNBH$_3$ was added and the pH was adjusted to ~5.0 with acetic acid. The mixture was stirred 12 hours, quenched with Na$_2$CO$_3$(sat), extracted with EtOAc, dried (Na$_2$SO$_4$), filtered and evaporated to give N-(isoquinolin-6-yl)-2-(3-chlorobenzylamino)acetamide (E59).

Using largely the procedures set forth in Examples 58-59 and substituting the appropriate starting materials, the compounds 60-63 were made.

| Example No. | n1 | n2 | R$^1$ |
|---|---|---|---|
| 60 | 0 | 0 | p-C$_6$H$_4$—CO$_2$Me |
| 61 | 0 | 0 | m-C$_6$H$_4$—F |
| 62 | 0 | 0 | m-C$_6$H$_4$—OAc |
| 63 | 0 | 0 | m-C$_6$H$_4$—OCF$_3$ |

Similarly, using largely the procedures set forth in Examples 58-59 and substituting the appropriate starting materials, the compounds 64-86 can be made.

| Example No. | n1 | n2 | R$^1$ |
|---|---|---|---|
| 64 | 0 | 0 | p-C$_6$H$_4$—OMe |
| 65 | 0 | 0 | o-C$_6$H$_4$—Cl |
| 66 | 0 | 0 | m-C$_6$H$_4$—CONHMe |
| 67 | 0 | 0 | (morpholinyl) |
| 68 | 0 | 0 | CH$_3$ |
| 69 | 0 | 0 | m-C$_6$H$_4$—CF$_3$ |
| 70 | 0 | 0 | p-C$_6$H$_4$—F |
| 71 | 0 | 0 | 1,2,4-C$_6$H$_2$—Cl$_3$ |
| 72 | 0 | 0 | 1,4-C$_6$H$_3$—Cl$_2$ |
| 73 | 0 | 0 | 2,4-C$_6$H$_3$—Cl$_2$ |
| 74 | 0 | 0 | (2-thienyl) |
| 75 | 0 | 0 | (3-thienyl) |
| 76 | 0 | 0 | (2-pyridyl) |
| 77 | 0 | 0 | (3-pyridyl) |
| 78 | 0 | 0 | (4-pyridyl) |
| 79 | 1 | 0 | o,p-C$_6$H$_3$—Cl$_2$ |
| 80 | 1 | 0 | m-C$_6$H$_4$—CO$_2$Me |
| 81 | 1 | 0 | o-C$_6$H$_4$—F |
| 82 | 1 | 0 | C$_6$H$_5$ |
| 83 | 2 | 0 | C$_6$H$_5$ |
| 84 | 0 | 1 | p-C$_6$H$_4$—Cl |
| 85 | 0 | 1 | p-C$_6$H$_4$CONHC$_6$H$_5$ |
| 86 | 0 | 1 | o-C$_6$H$_5$ |

EXAMPLE 87

Preparation of benzylisoquinolin-6-ylcarbamate (E87)

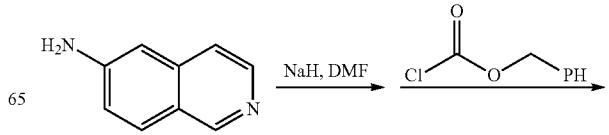

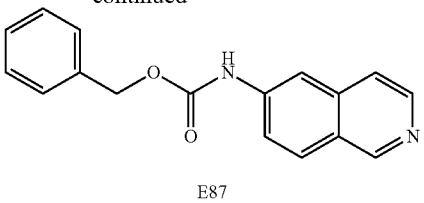

E87

To 6-aminoisoquinoline in DMF at −40° C. was added NaH and solution was warmed to 0° C. for 30 minutes. Then benzylchloroformate was added and the reaction stirred at 0° C. for 2 hours. The solution was quenched with AcOH, poured into NaHCO$_3$(sat) and extracted with EtOAc, dried (Na$_2$SO$_4$), filtered and evaporated. Flash chromatography (SiO$_2$ 90% EtOAc/Hex) gave benzylisoquinolin-6-ylcarbamate. (E87).

EXAMPLE 88

Preparation of 1-benzyl-3-(isoquinolin-6-yl)urea (E88)

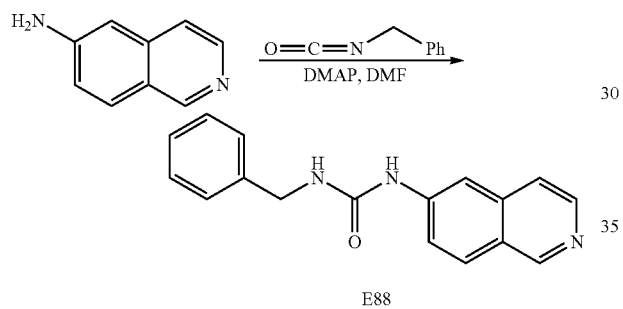

E88

To 6-aminoisoquinoline in DMF is added DMAP and benzyl isocyanate and the solution was stirred at room temperature for 4 hours. The mixture was poured into NaHCO$_3$ (sat), extracted with EtOAc, dried (Na$_2$SO$_4$), filtered and evaporated. Flash chromatography (SiO$_2$, 5% MeOH/CH$_2$Cl$_2$) provided 1-benzyl-3-(isoquinolin-6-yl) urea (E88).

Using largely the procedures set forth in Examples 87-88 and substituting the appropriate starting materials, the compounds 89-98 were made.

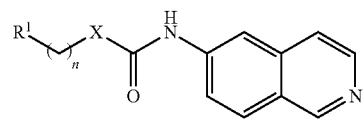

| Example No. | n | X  | R$^1$ |
|---|---|---|---|
| 89 | 0 | O  | p-C$_6$H$_4$—OMe |
| 90 | 0 | NH | o-C$_6$H$_4$—CH$_2$C$_6$H$_5$ |
| 91 | 0 | NH | m-C$_6$H$_4$—CH$_2$C$_6$H$_5$ |
| 92 | 0 | NH | p-C$_6$H$_4$—CH$_2$C$_6$H$_5$ |
| 93 | 0 | NH | C$_6$H$_5$ |
| 94 | 0 | NH | p-C$_6$H$_4$—Cl |
| 95 | 1 | O  | o-C$_6$H$_4$—Cl |
| 96 | 1 | NH | o-C$_6$H$_4$—Cl |

| Example No. | n | X  | R$^1$ |
|---|---|---|---|
| 97 | 1 | NH | 2-furyl-CH< |
| 98 | 2 | O  | —OCH$_2$CH$_2$C$_6$H$_5$ |

Similarly, using largely the procedures set forth in Examples 87-88 and substituting the appropriate starting materials, the compounds 99-104 can be made.

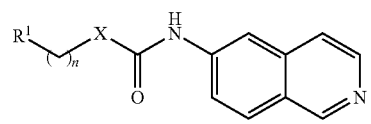

| Example No. | n | X  | R1 |
|---|---|---|---|
| 99  | 0 | O  | C$_6$H$_5$ |
| 100 | 0 | O  | m-C$_6$H$_4$—Cl |
| 101 | 0 | O  | m-C$_6$H$_4$—F |
| 102 | 0 | NH | 2,6-dichloropyridin-4-yl |
| 103 | 1 | NH | m-C$_6$H$_4$—CONHMe |
| 104 | 1 | NH | p-C$_6$H$_4$—Cl |

EXAMPLE 105

Preparation of N-(isoquinolin-6-yl)-2-morpholinoacetamide. (E105)

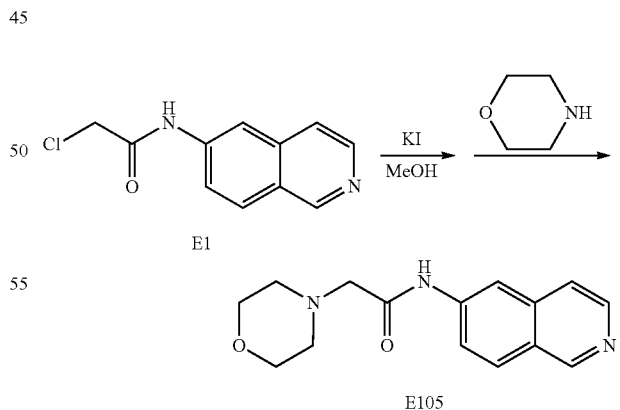

To 2-chloro-N-(isoquinolin-6-yl)acetamide (E1) in MeOH is added KI and the solution is heated to 60° C. for 40 minutes. The mixture is cooled to 45° C. and morpholine is added and stirred at 45° C. After 2-4 hours, the solvents are evaporated and the residue is taken up in EtOAc and extracted with NaHCO$_{3(sat)}$. The organics are dried (Na$_2$SO$_4$), filtered and evaporated. Flash chromatography (2% NH₃(2M)/MeOH/ 3% MeOH/CH₂Cl₂) gives N-(isoquinolin-6-yl)-2-morpholino acetamide (E105).
Using largely the procedure set forth in Example 105 and substituting the appropriate starting materials, the compounds 106-116 can be made.
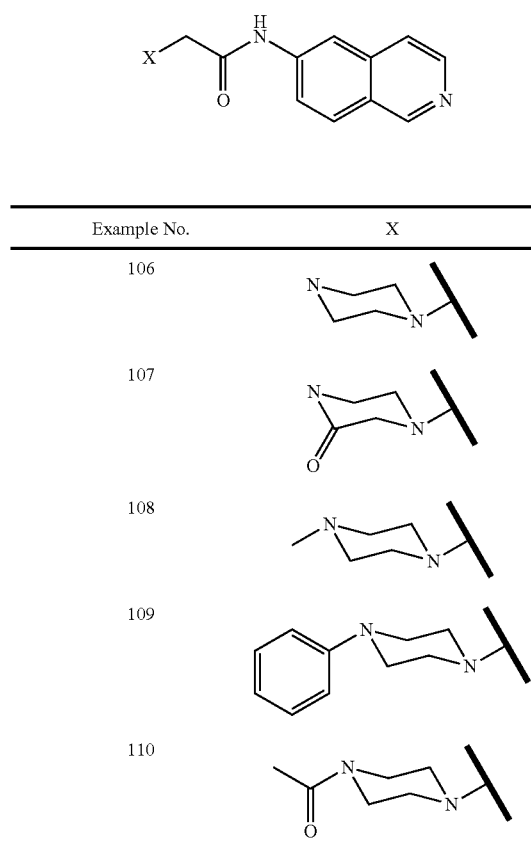
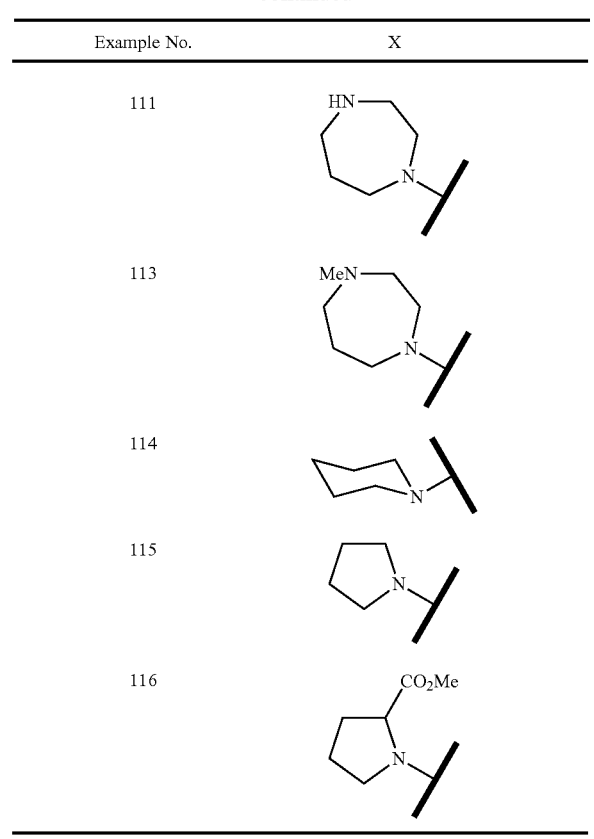
EXAMPLE 117
Synthesis of 4-(2-(isoquinolin-6-ylcarbamoyl)cyclopropyl)-N-(4-phenoxyphenyl)benzamide: (E117d)
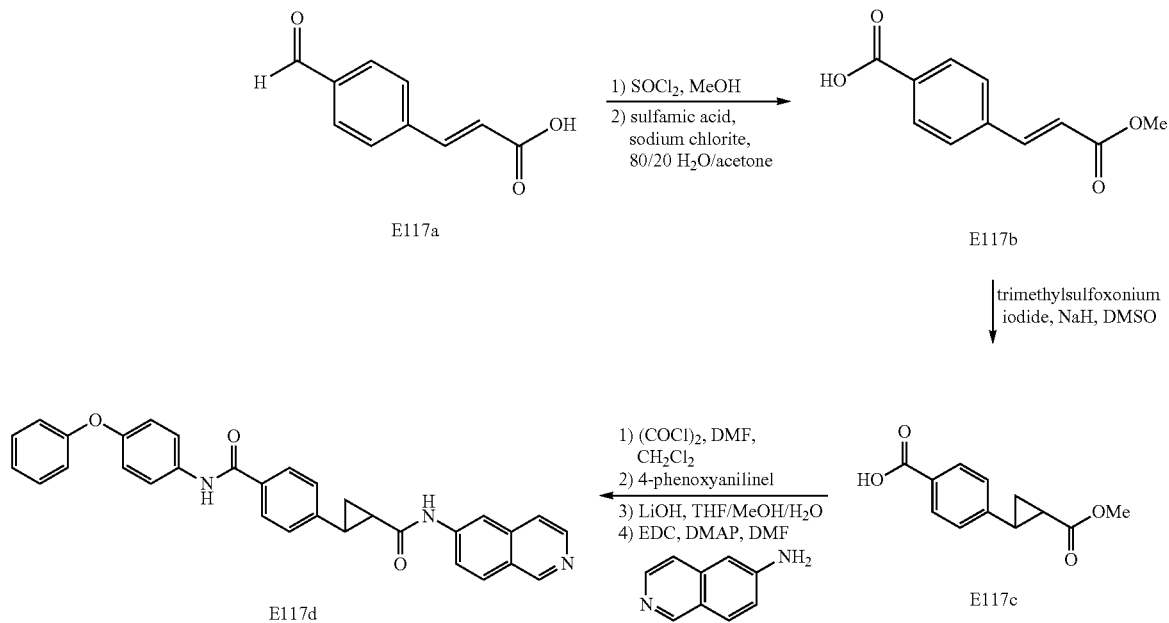

A stirred suspension of 4-formylcinnamic acid (58.3 mmol) in 130 mL methanol was protected from the atmosphere with a CaCl$_2$ guard tube attached to the end of a condenser. The reaction mixture was maintained between −50 and −45° C. [dry ice/acetone] while thionyl chloride (3 equiv.) was added over 1 h using syringe pump (addition rate: 0.25 ml/min) During addition the reaction thickened but stirring continued. Following addition, the reaction was allowed to stir and come to room temperature overnight. Volatiles were removed under reduced pressure (Rotovap). Dichloromethane was added. The reaction was stirred and water was carefully added. The mixture was transferred to a separatory funnel. The aqueous layer was removed and discarded. The organic phase was washed consecutively with brine, sat. NaHCO$_3$ and brine. The organic phase was dried over MgSO$_4$, filtered and concentrated. The solid was recrystallized from CH$_2$Cl$_2$/hexanes to provide the intermediate methyl ester.

The methyl ester (9.31 mmol) was dissolved in 300 ml acetone then diluted with 75 ml water. To this suspension, the sulfamic acid (1.45 eq.) and sodium chlorite (1.40 eq.) were added. The reaction stirred at room temperature for three hours. The reaction mixture was extracted with EtOAc and the combined organic extracts were dried over MgSO$_4$, filtered and concentrated. The material was recrystallized from EtOAc to give the intermediate acid, E117b.

2.2 eq NaH (60% dispersion in oil) and 2.5 eq trimethylsulfoxonium iodide were weighed into a dry flask under nitrogen. 20 ml anhydrous DMSO was added and the reaction stirred one hour at room temperature. The intermediate acid E117b (6.8 mmol), dissolved in 6 ml anhydrous DMSO was added dropwise. After 2.5 hours at room temperature, the reaction was poured into 1N HCl and extracted with EtOAc. The combined organic layers were washed with a minimal amount of aqueous sodium thiosulfate then brine. The combined organic layers were then dried over MgSO$_4$, filtered and concentrated to provide the intermediate cyclopropane E117c. The material E117c was used without further purification.

The intermediate cyclopropane (0.95 mmol) was dissolved in 5 ml anhydrous CH$_2$Cl$_2$ under nitrogen. Two drops of anhydrous DMF were added followed by 1.1 eq. of oxalyl chloride. After 1.5 hours, this solution was added dropwise to a solution of 1.0 eq. of 4-phenoxyaniline and 1.2 eq. Et$_3$N dissolved in 5 ml CH$_2$Cl$_2$. The reaction was left at room temperature overnight then poured into water. The aqueous layer was extracted with CH$_2$Cl$_2$. The combined organic layers were dried over MgSO$_4$, filtered and concentrated. The intermediate amide was purified by flash chromatography.

The intermediate amide (0.125 mmol) was dissolved in 1.2 ml of 3:1 THF/MeOH. 3 Eq. of LiOH.H$_2$O dissolved in 300 μL water was added to this solution at 0° C. The reaction was warmed to room temperature. After one hour the reaction was quenched with sat. NH$_4$Cl then the pH lowered to 3 with 1N HCl. The precipitate was either collected by filtration or the aqueous layer was extracted with EtOAc. The combined organic extracts were dried over MgSO$_4$, filtered and concentrated to give the intermediate acid. The material was used without further purification.

The intermediate acid was dissolved in 1 mL anhydrous DMF under nitrogen. 1.6 eq. EDC was added followed by 0.08 eq. DMAP and 1.3 eq. 6-aminoisoquinoline and the reaction left at room temperature over night. Reaction was poured into water and extracted with EtOAc. The combined organic layers were washed once with water, dried over MgSO$_4$, filtered and concentrated. The final compound E117d was purified by flash chromatography.

EXAMPLE 118

Synthesis of 4-(2-(isoquinolin-6-ylcarbamoyl)cyclopropyl)-N-(pyridin-4-yl)benzamide (E118)

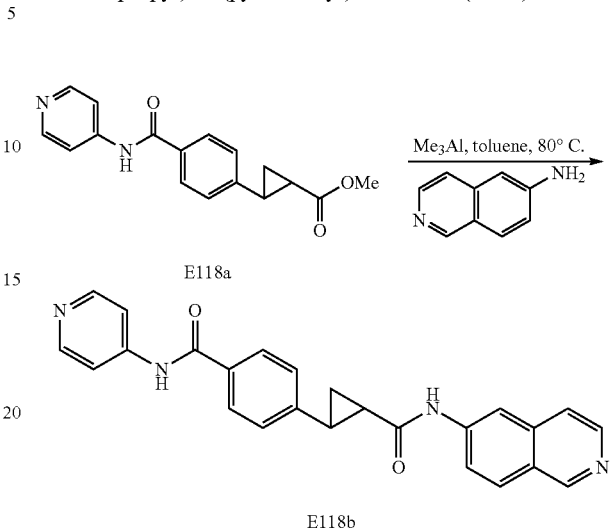

Using the procedures in Example 117, Intermediate 118a was prepared. 1.2 Eq. of 6-aminoisoquinoline was suspended in 0.5 ml toluene in a dry flask under nitrogen. 1.2 eq of 2.0M trimethylaluminum in heptane was added dropwise. After one hour all the suspended material has dissolved. This solution was added to 0.1 mmol of intermediate 118a suspended in 0.5 ml toluene under nitrogen. The reaction is heated at 80° C. overnight. Sat. aq. Rochelle's salt was added to the reaction and this was stirred vigorously for 30 minutes. The aqueous layer was extracted with EtOAc and the combined organic extracts were dried over MgSO$_4$, filtered and concentrated. The compound E118b was purified by flash chromatography.

REFERENCE EXAMPLE ONE

The Cell-Based Porcine Trabecular Meshwork (PTM) Assay

The anterior section of porcine eyes was harvested within 4 hours post-mortem. The iris and ciliary body were removed and trabecular meshwork cells were harvested by blunt dissection. Finely minced trabecular meshwork tissue was plated into collagen-coated 6-well plates in Medium-199 containing 20% fetal bovine serum (FBS). After two passages at confluence, cells were transferred to low-glucose DMEM containing 10% FBS. Cells were used between passage 3 and passage 8.

Cells were plated into fibronectin-coated, glass multiwell plates the day before compound testing under standard culture conditions. Compounds were added to cells in the presence of 1% FBS-containing DMEM and 1% DMSO. When compounds were incubated with the cells for the duration determined to be optimal, the media and compound is removed and cells fixed for 20 minutes in 3% methanol-free paraformaldehyde. Cells were rinsed twice with phosphate buffered saline (PBS) and cells are permeabilized with 0.5% Triton X-100 for two minutes. Following an additional two washes with PBS, F-actin was stained with Alexa-fluor 488-labelled phalloidin and nuclei are stained with DAPI.

Data was reduced to the mean straight actin-fiber length and normalized to DMSO-treated control cells (100%) and 50

μM Y-27632 (0%). Y-27632 is a rho-kinase inhibitor known to result in the depolymerization of F-actin in these cells

EXAMPLE 119

Preparation of 2-chloro-N-(5-chloro-isoquinolin-6-yl) acetamide. (E119a) and 3-(2-(5-chloro isoquinolin-6-ylamino)-2-oxo ethylamino)-N-methyl benzamide. (E119b)

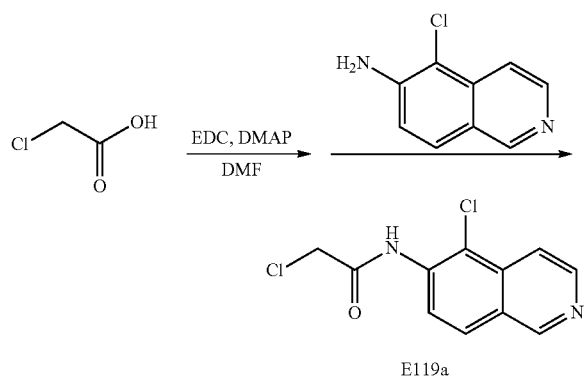

E119a

To chloroacetic acid in DMF is added EDC, DMAP and 5-chloro-6-aminoisoquinoline. This mixture is stirred for 4 hours. The reaction is washed with NaHCO$_3$(sat), extracted with EtOAc, dried (Na$_2$SO$_4$), filtered and evaporated. Column chromatography (SiO$_2$, 5% MeOH/CH$_2$Cl$_2$) gives 2-chloro-N-(5-chloro-isoquinolin-6-yl) acetamide.

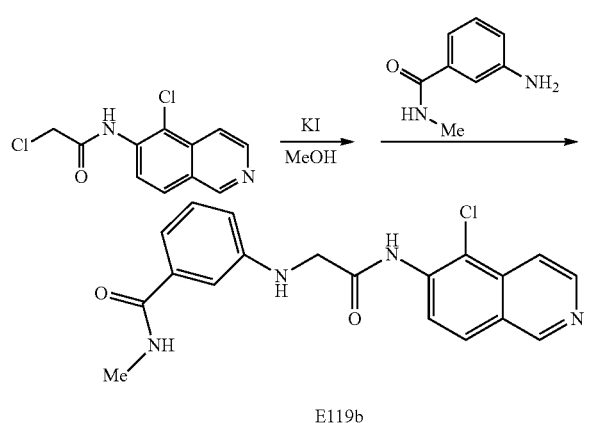

E119b

To 2-chloro-N-(5-chloroisoquinolin-6-yl) acetamide in MeOH is added KI and the solution is heated to 60° C. for 40 minutes. The mixture is cooled to 45° C. and 3-amino-N-methylbenzamide is added and stirred at 45° C. After 2-4 hours or when TLC indicates completion of the reaction, the solvents are evaporated and the residue is taken up in EtOAc and extracted with NaHCO$_3$ (sat). The organics are dried (Na$_2$SO$_4$), filtered and evaporated. Flash chromatography (SiO$_2$, NH$_3$(2M) in MeOH/3% MeOH/CH$_2$Cl$_2$) gives pure 3-(2-(5-chloroisoquinolin-6-ylamino)-2-oxoethylamino)-N-methylbenzamide.

Using the general procedure shown for example 119b, the following compounds can be synthesized from the corresponding 6-aminoisoquinoline.

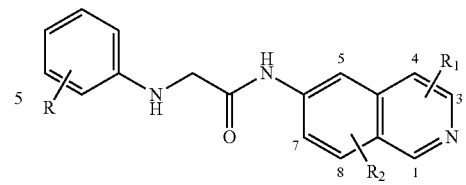

| Example | R | R2 | R1 |
|---|---|---|---|
| 120 | 3-CONHMe | 5-Cl | H |
| 121 | 3-CONHMe | 5-Br | H |
| 122 | 3-CONHMe | 5-Me | H |
| 123 | 3-CONHMe | 5-nPr | H |
| 124 | 3-CONHMe | 5-CH=CH$_2$ | H |
| 125 | 3-CONHMe | 5-CH2CH=CH$_2$ | H |
| 126 | 3-CONHMe | 5,8-diMe | H |
| 127 | 3-CONHMe | 7-Me | 1-Cl |
| 128 | 3-COMe | 5-Cl | H |
| 129 | 3-COMe | 5-Me | H |
| 130 | 3-CO$_2$Me | 5-Cl | H |
| 131 | 3-CO$_2$Me | 5-Me | H |
| 132 | 3-Cl | 5-Cl | H |
| 133 | 3-Cl | 5-Me | H |
| 134 | 3-OMe | 5-Cl | H |
| 135 | 3-OMe | 5-Me | H |

EXAMPLE 136

Preparation of 3-((N-isoquinolin-6-ylsulfamoyl)methylamino)-N-methylbenzamide. (E136)

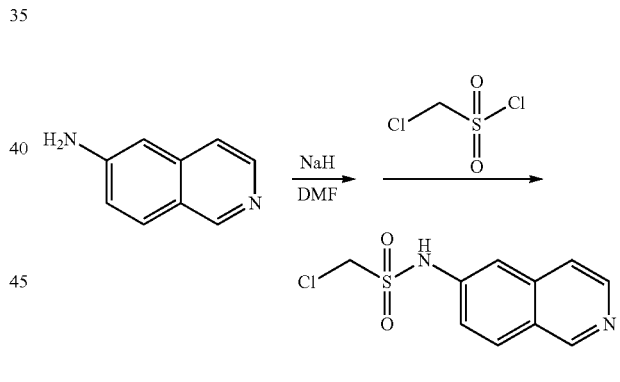

To 6-aminoisoquinoline in DMF at 0° C. is added NaH. After 30 min, chlorosulfonyl chloride is added to the reaction. After 2-4 hours at rt or when TLC indicates completion, the reaction is quenched by the addition of water and extracted with EtOAc. The combined organics are washed with brine and dried (Na$_2$SO$_4$), filtered and evaporated. Column chromatography (SiO$_2$, 5% MeOH/CH$_2$Cl$_2$) gives 1-chloro-N-(isoquinolin-6-yl) methanesulfonamide.

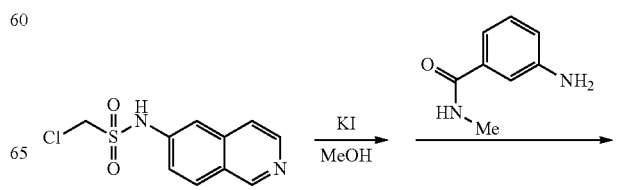

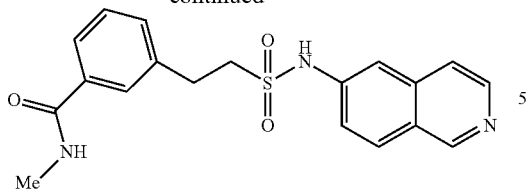

To 1-chloro-N-(isoquinolin-6-yl) methanesulfonamide in MeOH is added KI and the solution is heated to 60° C. for 40 minutes. The mixture is cooled to 45° C. and 3-amino-N-methylbenzamide is added and stirred at 45° C. After 2-4 hours or when TLC indicated completion of the reaction, the solvents are evaporated and the residue is taken up in EtOAc and extracted with $NaHCO_3$ (sat). The organics are dried ($Na_2SO_4$), filtered and evaporated. Flash chromatography ($SiO_2$, 2% $NH_3$(2M) in MeOH/3% $MeOH/CH_2Cl_2$) gives 3-((N-isoquinolin-6-ylsulfamoyl)methylamino)-N-methyl-benzamide.

EXAMPLES 137-141

Using the General Procedure Shown for Example 136, the Following Compounds can be Synthesized from the Corresponding 6-aminoisoquinoline

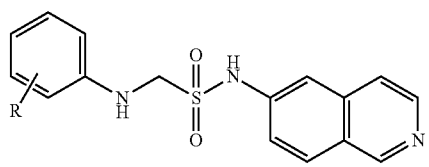

| Example | R |
|---|---|
| 137 | 3-$CONH_2$ |
| 138 | 3-COMe |
| 139 | 3-$CO_2$Me |
| 140 | 3-Cl |
| 141 | 3-OMe |

EXAMPLE 142

Using the General Procedure Shown for Example 119, the Following Compound was Synthesized from the Corresponding Cycloalkylamine

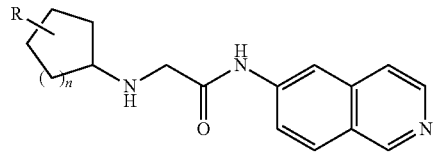

| Example No. | n | R |
|---|---|---|
| 142 | 2 | H |

EXAMPLES 143-147

Using the General Procedure Shown for Example 119, the Following Compounds could be Synthesized from the Corresponding Cycloalkylamines

| Example No. | n | R |
|---|---|---|
| 143 | 1 | H |
| 144 | 2 | 3-CONHMe |
| 145 | 2 | 3-$CO_2$Me |
| 146 | 2 | 3-COMe |
| 147 | 2 | 3-Cl |

EXAMPLE 148

Preparation 2-(4-(1-(4-chlorobenzyl)-1H-1,2,3-triazol-4-yl)phenoxy)-N-(isoquinolin-6-yl)-acetamide (E148)

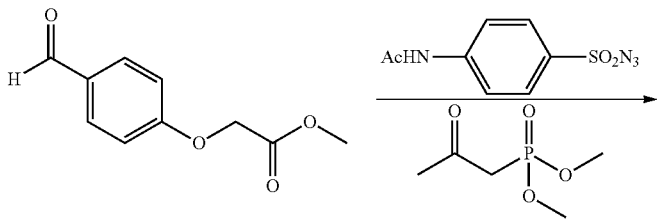

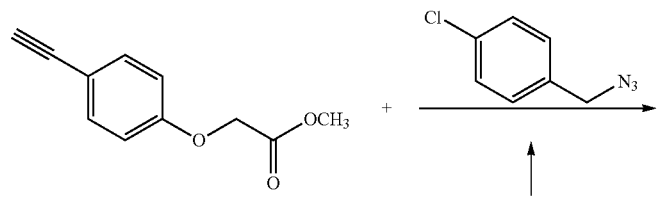

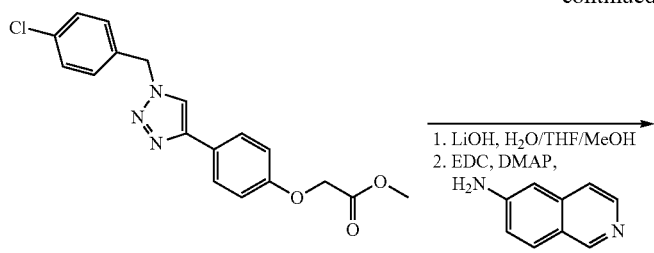
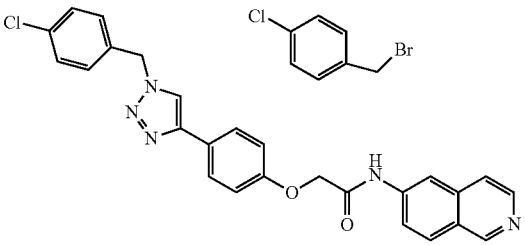

E148

A solution of 4-acetamidobenzenesulfonyl azide in acetonitrile was treated with cesium carbonate and stirred at room temperature for 5 minutes. Dimethyl 2-oxopropylphosphonate was added and stirred for 1 hour. Then, a solution of methyl 2-(4-formylphenoxy)acetate in MeOH was added to the reaction and stirred for an additional 2 hours. The solvents were removed and the residue was dissolved in diethyl ether and washed with water and brine. The organics were dried ($Na_2SO_4$), filtered and concentrated. Flash chromatography ($SiO_2$, EtOAc/hexanes) gave the corresponding alkyne.

A solution of 4-chlorobenzyl bromide in acetone was treated with $NaN_3$ and refluxed for 3 hours. The reactions was concentrated by 50% and diluted with saturated sodium chloride solution. The reaction was then extracted with $Et_2O$, washed with brine, dried ($Na_2SO_4$) and concentrated to give 1-(azidomethyl)-4-chlorobenzene.

A 5 mL microwave reaction vial was charged with methyl 2-(4-ethynylphenoxy)acetate, 1-(azidomethyl)-4-chlorobenzene, t-BuOH, copper turnings and copper sulfate. The reaction was heated under microwave conditions at 125° C. for 25 minutes. The reaction was cooled to room temperature and poured into water. The reaction was extracted with $CH_2Cl_2$. The combined organic layers were washed with water, dried ($Na_2SO_4$), filtered and concentrated. Flash chromatography ($SiO_2$, Hexanes/EtOAc) gave 2-(4-(1-(4-chlorobenzyl)-1H-1,2,3-triazol-4-yl)phenoxy)-N-(isoquinolin-6-yl)-acetamide (E148).

EXAMPLE 149

Preparation of 2-(4-(1-benzyl-1H-tetrazol-5-yl)phenoxy-N-(isoquinolin-6-yl)acetamide (E149)

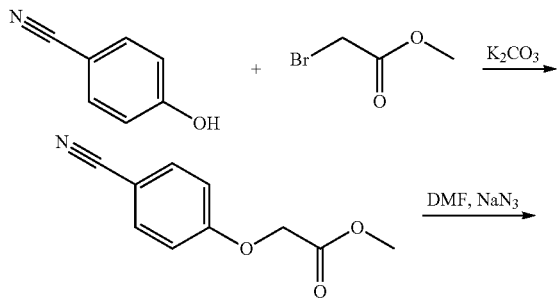

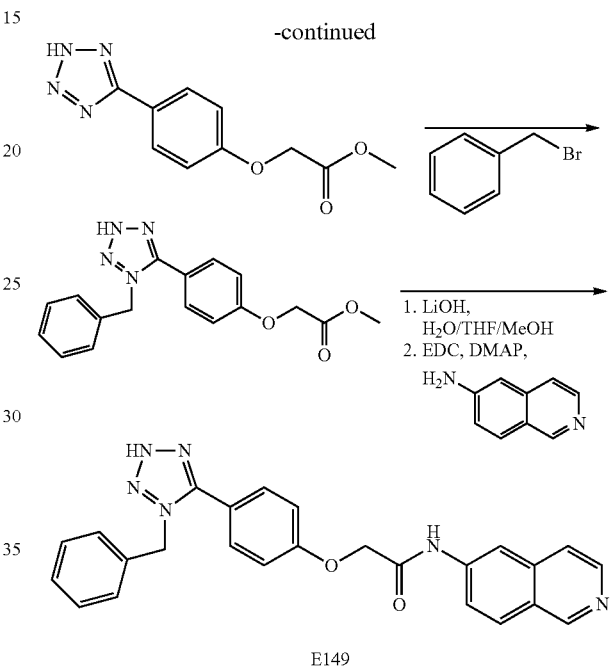

E149

A mixture of 4-cyanophenol and methyl bromoacetate in $CH_3CN$ was treated with $K_2CO_3$ and refluxed for 18 hours. Then the reaction was cooled to room temperature and concentrated. The residue was partitioned between EtOAc and $H_2O$ and the organic layer was washed with brine, driend ($Na_2SO_4$), filtered and evaporated. Flash chromatography ($SiO_2$, hexanes/EtOAc) gave pure methyl 2-(4-cyanophenoxy)acetate.

A solution methyl 2-(4-cyanophenoxy)acetate in DMF was treated with $NaN_3$ and $NH_4Cl$ and stirred in an oil bath at 80° C. for 18 hours. Then, the mixture was poured into $H_2O$ and extracted with $Et_2O$. The aqueous layer was acidified to pH 2-3 with HCl and the precipitate was collected to give methyl 2-(4-(2H-tetrazol-5-yl)phenoxy)acetate.

A solution of methyl 2-(4-(2H-tetrazol-5-yl)phenoxy)acetate in acetone was treated with triethylamine and stirred at room temperature for 20 minutes. Benzyl bromide was added and stirred for 18 hours at 60° C. The solvent was removed and the residue was purified by reverse phase preparative HPLC to give 2-(4-(1-(4-chlorobenzyl)-1H-1,2,3-triazol-4-yl)phenoxy)-N-(isoquinolin-6-yl)-acetamide (E149).

Using largely the procedures set forth in Examples 148-149 and substituting the appropriate starting material, the compounds 150-153 were made.

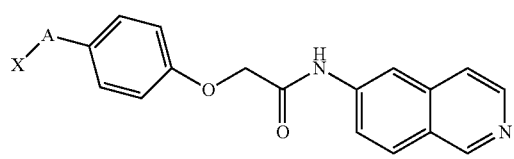

| Example No. | A | X |
|---|---|---|
| 150 | [1,2,3-triazole] | m-CH$_2$—C$_6$H$_4$—F |
| 151 | [1,2,3-triazole] | m-CH$_2$—C$_6$H$_4$—OMe |
| 152 | [1,2,3-triazole] | o-CH$_2$—C$_6$H$_4$—CH$_3$ |
| 153 | [tetrazole] | m-CH$_2$—C$_6$H$_4$—OMe |

EXAMPLE 154

Using Largely the Procedure set Forth in Examples 117 and 118 and Substituting the Appropriate Starting Materials the Compounds 154-157 were Made

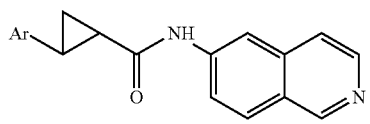

| Example | Ar |
|---|---|
| 154 | Ph— |

155

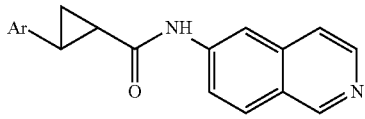

| Example | Ar |
|---|---|
| 156 | 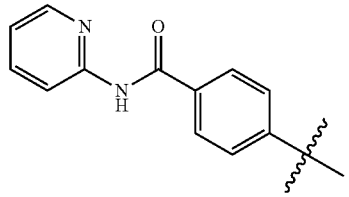 [SMILES: *c1ccc(C(=O)Nc2ccccn2)cc1] |
| 157 | 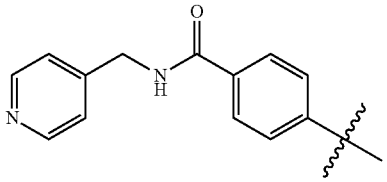 [SMILES: *c1ccc(C(=O)NCc2ccncc2)cc1] |

EXAMPLE 158-169

Using Essentially the Procedure set Forth in Examples 117 and 118 and Substituting the Appropriate Starting Materials the Compounds 158-169 can be Made

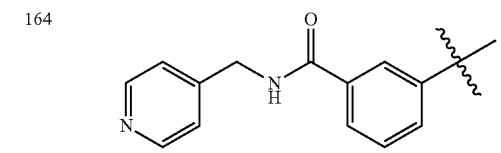

| Example | Ar |
|---|---|
| 158 | m-F—C$_6$H$_4$ |
| 159 | m-MeO—C$_6$H$_4$ |
| 160 | m-COOMe—C$_6$H$_4$ |
| 161 | 2-pyridyl |
| 162 | 3-pyridyl |
| 163 | 4-pyridyl |
| 164 | |
| 165 | 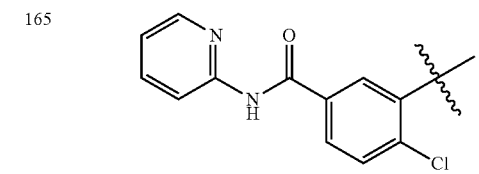 |
| 166 | 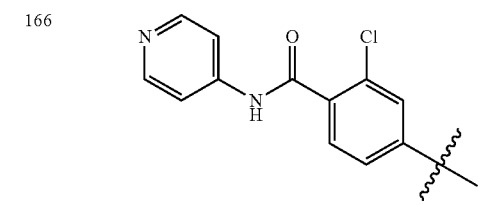 |

| Example | Ar |
|---|---|
| 167 | 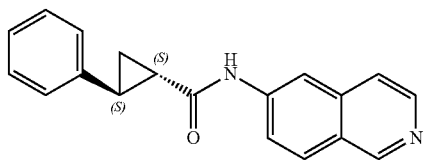 |

EXAMPLE 168

Synthesis of (1S,2S)-N-(isoquinolin-6-yl)-2-phenyl-cyclopropane carboxamide: (E168)

The title compound is obtained as described in Example 117.

EXAMPLE 169

Synthesis of (1R,2R)—N-(isoquinolin-6-yl)-2-phenylcyclopropane carboxamide (E169)

The title compound is obtained as described in Example 117.

The chiral non-racemic materials described in these examples may be obtained by following the references set herein: Resolution of trans-phenylcyclopropane carboxylic acids via the quinine salt: Inouye, Y.; Sugita, T.; Walborsky, H. M. *Tetrahedron* 1964, 20, 1695; Webster, F. X.; Zeng, X.; Silverstein, R. M. *J. Org. Chem.* 1982, 47, 5225, and references cited therein. Reference for resolution of trans-phenylcyclopropane carboxylic acids via separation on a chiral HPLC column: Penmetsa, K. V.; Reddick, C. D.; Fink, S. W.; Kleintop, B. L.; DiDonato, G. C.; Volk, K. J.; Klohr, S. E. *J. Liq. Chrom. & Rel. Technol.* 2000, 23, 831., and references cited therein.

EXAMPLES 170-178

Using Largely the Procedure set Forth in Examples 117 and 118 but Replacing the Cyclopropanation with a Hydrogenation and Substituting the Appropriate Starting Materials the Compounds 170-178 were Made

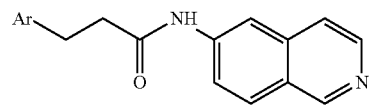

| Example | Ar |
|---|---|
| 170 | o-NH₂Ph— |
| 171 | |
| 172 | |
| 173 | |
| 174 | |
| 175 | |
| 176 | |

| Example | Ar |
|---|---|
| 177 | 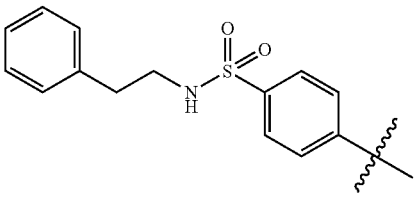 [SMILES: *c1ccc(S(=O)(=O)NCCc2ccccc2)cc1] |
| 178 | 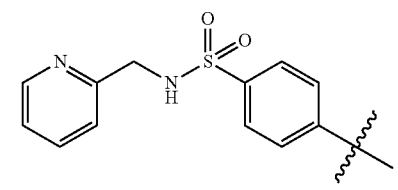 [SMILES: *c1ccc(S(=O)(=O)NCc2ccccn2)cc1] |

EXAMPLE 179-186

Using Largely the Procedure set Forth in Examples 117 and 118 but Replacing the Cyclopropanation with a Hydrogenation and Substituting the Appropriate Starting Materials the Compounds 179-186 can be Made

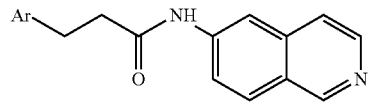

| Example | Ar |
|---|---|
| 179 | p-F—$C_6H_4$ |
| 180 | m-CN—$C_6H_4$ |
| 181 | m-$CF_3$—$C_6H_4$ |
| 182 | m-$NMe_2$—$C_6H_4$ |
| 183 | o-F—$C_6H_4$ |
| 184 | p-SMe—$C_6H_4$ |
| 185 | 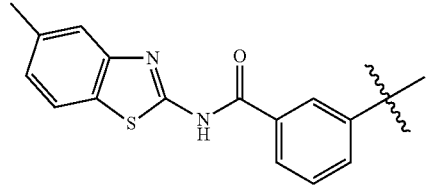 [SMILES: *c1cccc(C(=O)Nc2nc3cc(C)ccc3s2)c1] |
| 186 | 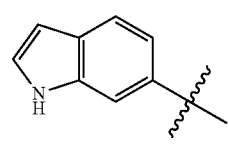 [SMILES: *c1ccc2cc[nH]c2c1] |

EXAMPLE 187-188

Using Largely the Procedure set Forth in Examples 117 and 118 but Eliminating the Cyclopropanation Step and Substituting the Appropriate Starting Materials the Compounds 187 and 188 were Made

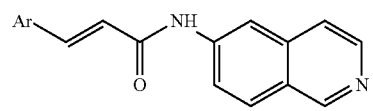

| Example | Ar |
|---|---|
| 187 | meta-$NH_2$Ph— |
| 188 | 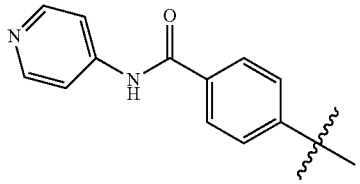 [SMILES: *c1ccc(C(=O)Nc2ccncc2)cc1] |

EXAMPLES 189-198

Using Largely the Procedure set Forth in Examples 117 and 118 but Eliminating the Cyclopropanation Step and Substituting the Appropriate Starting Materials the Compounds 189-198 can be Made

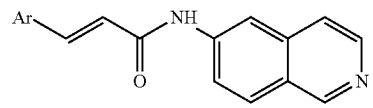

| Example | Ar |
|---|---|
| 189 | m-Cl—$C_6H_4$ |
| 190 | p-COOMe—$C_6H_4$ |
| 191 | 2-furan |
| 192 | 3-furan |
| 193 | 2-thiophene |
| 194 | 3-thiophene |
| 195 | p-COMe—$C_6H_4$ |
| 196 | m-$NO_2$—$C_6H_4$ |
| 197 | m-$NH_2$—$C_6H_4$ |
| 198 | m-OAc—$C_6H_4$ |

EXAMPLES 199-204

Using Largely the Procedure set Forth in Examples 117 and 118 and Substituting the Appropriate Starting Materials the Compounds 199-204 can be Made

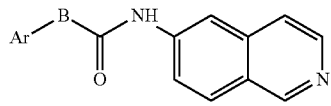

| Example | Ar | B |
|---------|-----|---|
| 199 | Ph— | |
| 200 | Ph— | |
| 201 | Ph— | —C≡C— |
| 202 | Ph— | C≡C—CH₂ |
| 203 | Ph— | trans-CH2—CH=CH— |
| 204 | Ph— | trans-CH=CH—CH₂— |

EXAMPLE 205

Synthesis of (E)-N-(isoquinolin-6-yl)-3-(4-(2-phenylacryloyl)phenyl) acrylamide (E205)

A round bottomed flask equipped with a condenser and a stirring bar was charged with benzyl 4-bromophenylketone (27 mmol), sodium acetate (1.2 eq) tert-butyl acrylate (1.2 eq) and N-methylpyrrolidinone (NMP) (35 ml). In a separate flask, 22.5 mg Pd(OAc)₂ was dissolved in 50 ml NMP. 6.75 ml of this solution was added to the reaction (0.05 mol %). The reaction mixture was heated to 135° C. for 40 minutes. After cooling to room temperature, the reaction was quenched with water then extracted with EtOAc. The combined organic layers were washed with water and brine and dried over Na₂SO₄. This solution was filtered though celite to removed the catalyst then concentrated to give the ester intermediate E205b. The material was used without further purification.

The ester intermediate E205b was dissolved in acetic anhydride (4 eq.) then N,N,N',N'-tetramethyldiaminomethane (2.5 eq) was added dropwise via syringe. After 40 minutes sat. NaHCO₃ was added and the resulting mixture extracted with EtOAc. The combined organic layers were washed with sat. NaHCO₃, 1N HCl and brine, dried over Na₂SO₄ and concentrated. The compound was purified by column chromatography to give the alkene intermediate E205c.

The alkene intermediate E205c (13.8 mmol) was dissolved in DCM and cooled to 0° C. 15 mL Trifluoroacetic acid was added and the reaction stirred at 0° C. for 1 hour then room temperature for 2 hours. The solvents were evaporated and the solid residue suspended in ether. Filtration gave the intermediate acid.

The intermediate acid (0.14 mmol) was dissolved in 0.8 ml anhydrous DMF under nitrogen. 1.6 Eq. EDC was added followed by 0.08 eq. DMAP and 1.3 eq. 6-aminoisoquinoline and the reaction left at room temperature for 3 hours. The reaction was poured into water and extracted with EtOAc. The combined organic layers were washed once with water, dried over Na₂SO₄, filtered and concentrated. The compound was purified by flash chromatography.

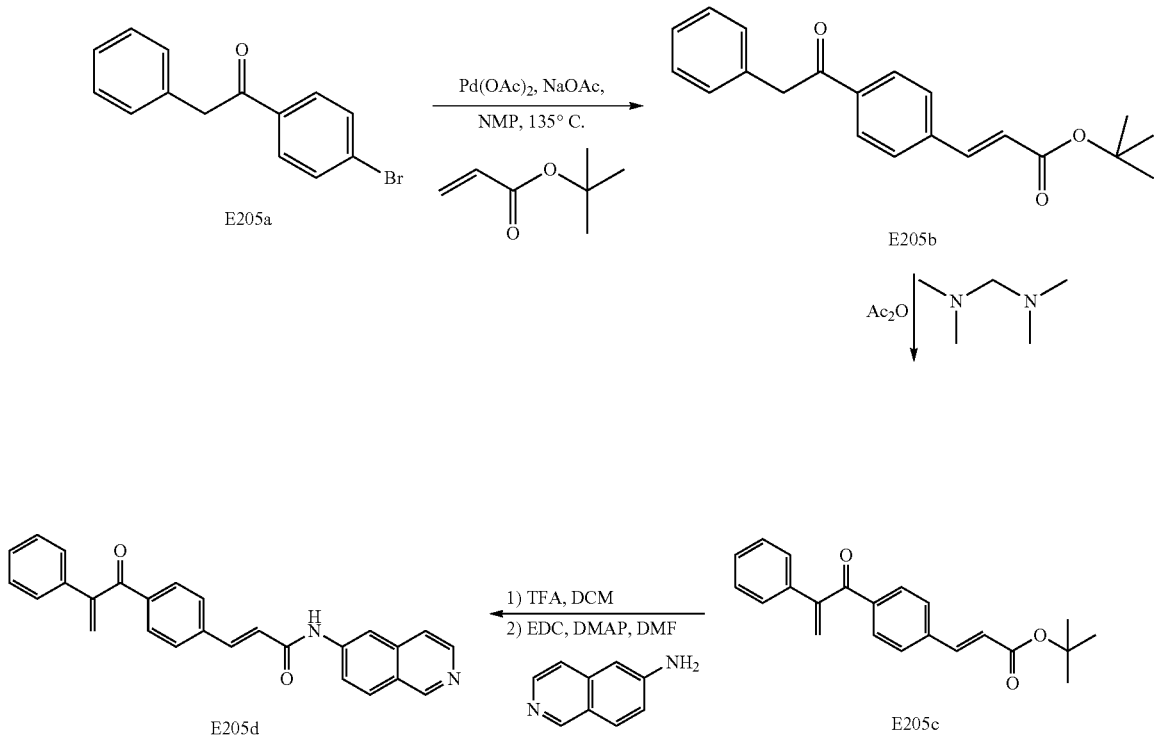

EXAMPLE 206

Synthesis of (E)-N-(isoquinolin-6-yl)-3-(4-(1-phenylcyclopropane carbonyl)phenyl) acrylamide (E206)

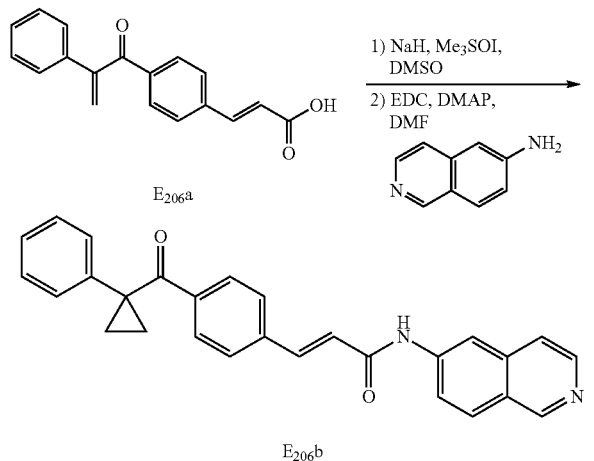

Using the procedure set forth in Example 205 intermediate E206a was made.

2.2 eq NaH (60% dispersion in oil) and 2.5 eq trimethylsulfoxonium iodide were weighed into a dry flask under nitrogen. Anhydrous DMSO was added and the reaction stirred one hour at room temperature. The intermediate acid E206a (0.36 mmol), dissolved in anhydrous DMSO was added dropwise. After 5 minutes at room temperature, the reaction was poured into 1N HCl and extracted with EtOAc. The combined organic layers were washed with a minimal amount of aqueous sodium thiosulfate then brine. The combined organic layers were then dried over MgSO$_4$, filtered and concentrated to provide the intermediate cyclopropane. The material was purified by flash chromatography to give the intermediate acid.

The intermediate acid (0.12 mmol) was dissolved in anhydrous DMF under nitrogen. 1.6 eq. EDC was added followed by 0.08 eq. DMAP and 1.3 eq. 6-aminoisoquinoline and the reaction left at room temperature for 3 hours. Reaction was poured into water and extracted with EtOAc. The combined organic layers were washed once with water, dried over MgSO$_4$, filtered and concentrated. The compound E206b was purified by flash chromatography.

EXAMPLE 207

Synthesis of (2R)-2-amino-3-(3-(4-((E)-3-(isoquinolin-6-ylamino)-3-oxoprop-1-enyl)phenyl)-3-oxo-2-phenylpropylthio)propanoic acid (E207)

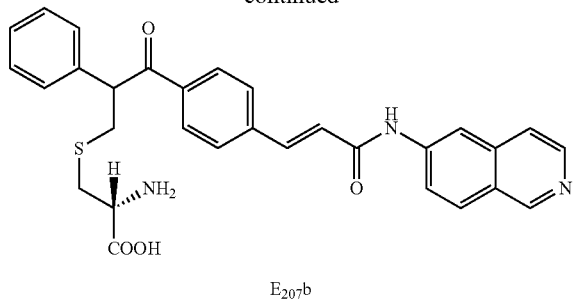

Intermediate E207a and (L)-cystine were suspended in 2:1 phosphate buffer/ACN. NaOH was added and the reaction stirred at room temperature. When reaction was complete by LC/MS, the pH was adjusted to 6. The precipitate that was formed was collected by filtration.

EXAMPLE 208

Synthesis of N-(isoquinolin-6-yl)-3-(4-(3-phenylpropanamido)phenyl) propanamide (E208b)

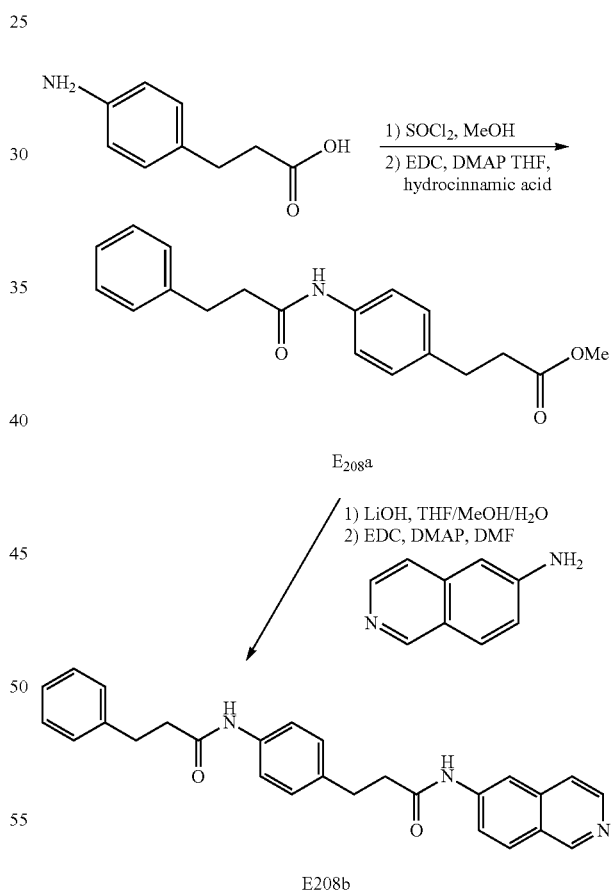

A solution of 3-(4-aminophenyl)propionic acid in methanol was cooled to 0° C. Thionyl chloride was added dropwise. Following addition, the reaction was heated to 40° C. overnight. The reaction was concentrated to provide the intermediate methyl ester which was used without further purification.

The intermediate ester (0.115) was dissolved in anhydrous THF under nitrogen. EDC was added followed by DMAP and hydrocinnamic acid. The reaction was left at room temperature over night. The reaction was poured into water and extracted with EtOAc. The combined organic layers were washed once with water, dried over MgSO₄, filtered and concentrated. The compound was purified by flash chromatography to give the intermediate amide (E208a).

The intermediate amide (E208a) was dissolved in 3:1 THF/MeOH. LiOH.H2O dissolved in water was added to this solution at 0° C. The reaction was warmed to room temperature. After one hour the reaction was quenched with sat. NH₄Cl then the pH lowered to 3 with 1N HCl. The precipitate was collected by filtration or the aqueous layer was extracted with EtOAc. The combined organic extracts were dried over MgSO₄, filtered and concentrated to give the intermediate acid. The material was used without further purification.

The intermediate acid was dissolved in anhydrous DMF under nitrogen. 1.6 eq. EDC was added followed by 0.08 eq. DMAP and 1.3 eq. 6-aminoisoquinoline and the reaction left at room temperature over night. Reaction was poured into water and extracted with EtOAc. The combined organic layers were washed once with water, dried over MgSO₄, filtered and concentrated. The compound (E208b) was purified by flash chromatography.

EXAMPLE 209

Synthesis of N-(4-(3-(isoquinolin-6-ylamino)-3-oxopropyl)phenyl)-4-methoxybenzamide (E209)

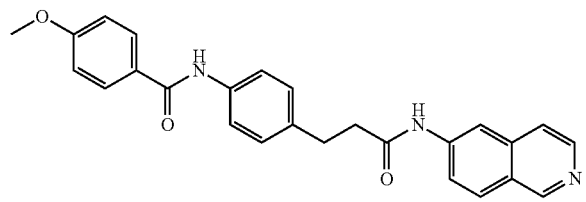 [SMILES: COc1ccc(C(=O)Nc2ccc(CCC(=O)Nc3ccc4cnccc4c3)cc2)cc1]

The title compound was obtained as described in Example 208

EXAMPLE 210

Synthesis of N-(isoquinolin-6-yl)-3-(4-(3-(3-(trifluoromethyl)phenyl) ureido)phenyl)propanamide (E110)

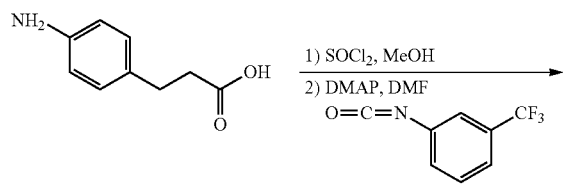

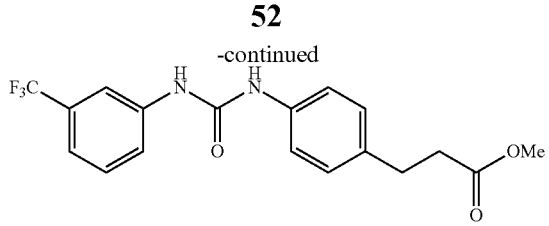

E₂₁₀a

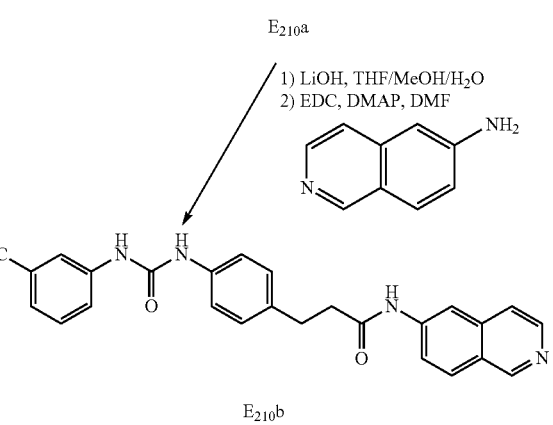

E₂₁₀b

Steps one, three and four were performed as in Example 208. Step two is performed as follows: To methyl 3-(4-aminophenyl)propanoate in DMF is added DMAP and 3-trifluoromethylphenyl isocyanate and the solution was stirred at room temperature for 4 hours. The mixture was poured into NaHCO₃ (sat), extracted with EtOAc, dried (Na₂SO₄), filtered and evaporated. The compound E210b was purified by flash chromatography.

EXAMPLE 211

Synthesis of (E)-3-(4-(3-(2-fluoro-5-methylphenyl)ureido)phenyl)-N-(isoquinolin-6-yl)acrylamide (E211)

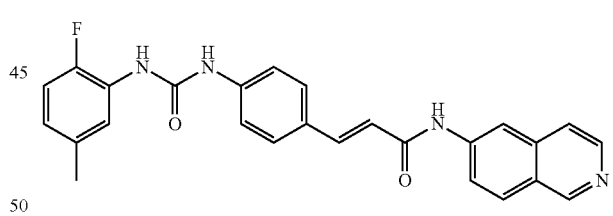

The title compound was obtained as described in Example 210.

REFERENCE EXAMPLE TWO

Pharmacological Activity for Glaucoma Assay

Pharmacological activity for glaucoma can be demonstrated using assays designed to test the ability of the subject compounds to decrease intraocular pressure. Examples of such assays are described in the following reference, incorporated herein by reference: C. Liljebris, G. Selen, B. Resul, J. Sternschantz, and U. Hacksell, "Derivatives of 17-Phenyl-18, 19, 20-trinorprostaglandin F₂α Isopropyl Ester: Potential Anti-glaucoma Agents", Journal of Medicinal Chemistry, Vol. 38 (2) 1995, pp. 289-304.

EXAMPLE 212

Topical pharmaceutical compositions for lowering intraocular pressure are prepared by conventional methods and formulated as follows:

| Ingredient | Amount (wt %) |
|---|---|
| 6-aminoisoquinoline Derivative | 0.50 |
| Dextran 70 | 0.1 |
| Hydroxypropyl methylcellulose | 0.3 |
| Sodium Chloride | 0.77 |
| Potassium chloride | 0.12 |
| Disodium EDTA | 0.05 |
| Benzalkonium chloride | 0.01 |
| HCl and/or NaOH | pH 7.0-7.2 |
| Purified water | q.s. to 100% |

A compound according to this invention is used as the 6-aminoisoquinoline derivative. When the composition is topically administered to the eyes once daily, the above composition decreases intraocular pressure in a patient suffering from glaucoma.

EXAMPLE 213

Example 212 is repeated using (2R)-2-amino-3-(3-(4-((E)-3-(isoquinolin-6-ylamino)-3-oxoprop-1-enyl)phenyl)-3-oxo-2-phenylpropylthio)propanoic acid (E207) according to this invention. When administered as a drop 4 times per day, the above composition substantially decreases intraocular pressure and serves as a neuroprotective agent.

EXAMPLE 214

Example 212 is repeated using 2-(benzylamino)-N-(isoquinolin-6-yl)acetamide (E58) according to this invention. When administered as a drop twice per day, the above composition substantially decreases intraocular pressure.

EXAMPLE 215

Example 212 is repeated using 2-chloro-N-(isoquinolin-6-yl) acetamide (E1) according to this invention. When administered as a drop twice per day, the above composition substantially decreases allergic symptoms and relieves dry eye syndrome.

EXAMPLE 216

Example 212 is repeated using 2-amino-N-isoquinoline-6-yl-acetamide dihydrochloride (E40) according to this invention. When administered as a drop as needed, the above composition substantially decreases hyperemia, redness and ocular irritation.

EXAMPLE 217

Example 212 is repeated using N-(isoquinolin-6-yl)-2-(3-methoxybenzylamino)acetamide (E59) according to this invention. When administered as a drop 4 times per day, the above composition substantially decreases intraocular pressure and serves as a neuroprotective agent.

EXAMPLE 218

Example 212 is repeated using 3-((N-isoquinolin-6-ylsulfamoyl)methylamino)-N-methylbenzamide (E136) according to this invention. When administered as a drop twice per day, the above composition substantially decreases intraocular pressure.

EXAMPLE 219

Example 212 is repeated using benzylisoquinolin-6-ylcarbamate (E87). according to this invention. When administered as a drop twice per day, the above composition substantially decreases allergic symptoms and relieves dry eye syndrome.

EXAMPLE 220

Example 213 is repeated using 1-benzyl-3-(isoquinolin-6-yl)urea (E88) according to this invention. When administered as a drop as needed, the above composition substantially decreases allergic symptoms

EXAMPLE 221

Example 213 is repeated using N-(isoquinolin-6-yl)-2-morpholinoacetamide (E105) according to this invention. When administered as a drop as needed, the above composition substantially decreases hyperemia, redness and ocular irritation.

EXAMPLE 222

Example 213 is repeated using 4-(2-(isoquinolin-6-ylcarbamoyl)cyclopropyl)-N-(pyridin-4-yl)benzamide (E118) according to this invention. When administered as a drop twice a day or as needed, the above composition substantially decreases intraocular pressure.

EXAMPLE 223

Example 213 is repeated using 3-(2-(5-chloroisoquinolin-6-ylamino)-2-oxoethylamino)-N-methylbenzamide (E119b) according to this invention. When administered as a drop twice a day or as needed, the above composition substantially decreases intraocular pressure.

While the invention has been described in detail and with reference to specific embodiments thereof, it will be apparent to one skilled in the art that various changes and modifications can be made without departing from the spirit and scope of the invention.

What is claimed is:

1. A compound according to Formula II:

(II)

wherein $R_1$ and $R_2$ are, independently, hydrogen, hydroxyl, halogen, $C_1$-$C_4$ alkyl, $C_2$-$C_4$ alkenyl, $C_2$-$C_4$ alkynyl, amino, nitro, cyano, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl or $C_1$-$C_4$ carboxyl;

wherein $R_4$ is hydrogen, halogen, alkyl, alkenyl, alkynyl, alkoxy, amino, cyano, cycloalkyl, heterocycloalkyl, aryl, $C_1$-$C_4$ alkyl aryl, heteroaryl, $C_1$-$C_4$ alkyl heteroaryl, carbonyl, carbonylamino, thioalkyl, sulfonyl, sulfonylamino, acyl, or carboxyl; and wherein B is a chain containing from 0 to 3 member atoms, X represents n independently chosen member atoms which together form a ring structure and n is an integer from about 1 to about 5.

2. The compound of claim 1, wherein B is a chain containing either 0 or 1 member atoms, X represents n independently chosen member atoms which together form a ring structure and n is an integer of from 1 to 4.

3. The compound according to claim 2, wherein $R_1$, and $R_2$ are, independently, hydrogen, hydroxyl, halogen, methyl, ethyl, amino, nitro or cyano.

4. The compound according to claim 3, wherein $R_4$ is alkyl, alkenyl, alkynyl, alkoxy, amino, cycloalkyl, heterocycloalkyl, aryl, $C_1$-$C_4$ alkyl aryl, heteroaryl, $C_1$-$C_4$ alkyl heteroaryl, acyl, or carboxyl.

5. The compound of claim 1, wherein n is 1.

6. The compound according to claim 1, wherein n is 1 and X is —CR'R'—, —NH—, or —O—; and wherein each R' is, independently, hydrogen, halogen, $C_1$-$C_4$ alkyl, $C_2$-$C_4$ alkenyl, $C_2$-$C_4$ alkynyl, amino, cyano, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl or $C_1$-$C_4$ carboxyl.

7. The compound according to claim 1, wherein X is —CR'R'— and B is zero, wherein each R' is, independently, hydrogen, halogen, $C_1$-$C_4$ alkyl, $C_2$-$C_4$ alkenyl, $C_2$-$C_4$ alkynyl, amino, cyano, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl or $C_1$-$C_4$ carboxyl.

8. The compound according to claim 7, wherein X is —CR'R'— wherein each R' is, independently, hydrogen, halogen, $C_1$-$C_4$ alkyl, amino, or cyano.

9. The compound according to claim 1, wherein $R_4$ is cycloalkyl, heterocycloalkyl, aryl, $C_1$-$C_4$ alkyl aryl, heteroaryl, or $C_1$-$C_4$ alkyl heteroaryl.

10. The compound according to claim 9, wherein $R_4$ is aryl and X is —CR'R'—; and wherein each R' is, independently, hydrogen, halogen, $C_1$-$C_4$ alkyl, amino or cyano.

11. The compound according to claim 1, wherein the compound is selected from the following:

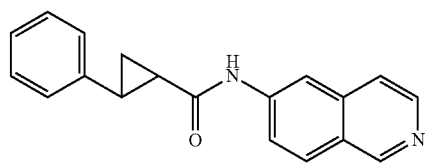

N-(isoquinolin-6-yl)-2-phenylcyclopropanecarboxamide

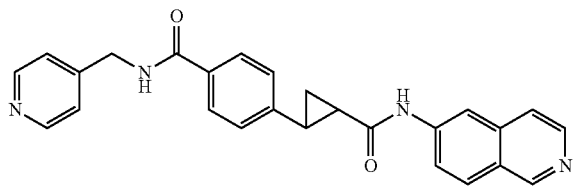

4-(2-(isoquinolin-6-ylcarbamoyl)cyclopropyl)-N-(pyridin-4-ylmethyl)benzamide

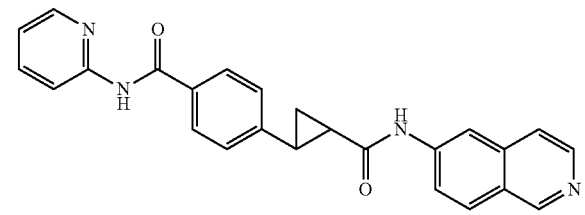

4-(2-(isoquinolin-6-ylcarbamoyl)cyclopropyl)-N-(pyridin-2-yl)benzamide

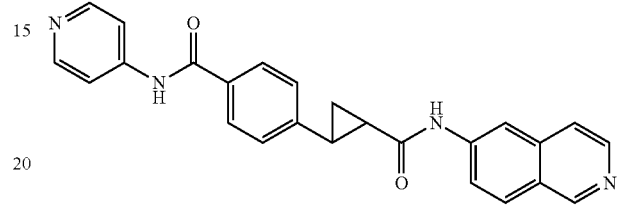

4-(2-(isoquinolin-6-ylcarbamoyl)cyclopropyl)-N-(pyridin-4-yl)benzamide

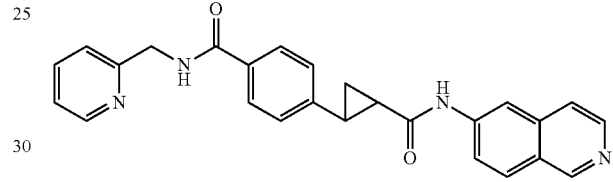

4-(2-(isoquinolin-6-ylcarbamoyl)cyclopropyl)-N-(pyridin-2-ylmethyl)benzamide

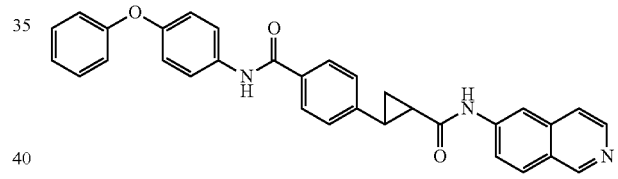

4-(2-(isoquinolin-6-ylcarbamoyl)cyclopropyl)-N-(4-phenoxyphenyl)benzamide

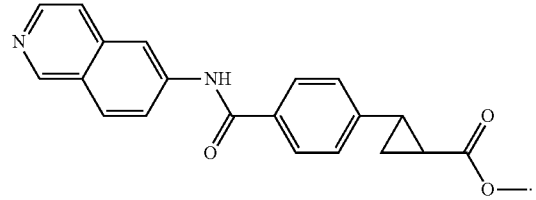

methyl 2-(4-(isoquinolin-6-ylcarbamoyl)phenyl)cyclopropanecarboxylate

12. A compound selected from the following:

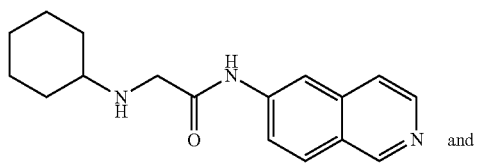

2-(cyclohexylamino)-N-(isoquinolin-6-yl)acetamide and

-continued

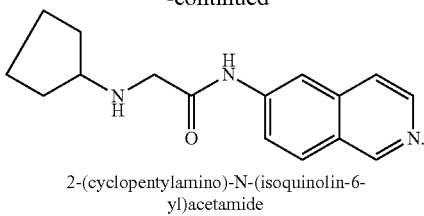

2-(cyclopentylamino)-N-(isoquinolin-6-yl)acetamide

13. A method for influencing the action of a kinase in a cell, a tissue, or a living mammal comprising administering to or contacting with the cell, tissue, or mammal at least one compound according to claim 1, or increasing the effectiveness of another therapeutic agent in a cell, tissue or living mammal comprising administering to or contacting with the cell, tissue or mammal a therapeutically effective amount of at least one compound according to claim 1.

14. The method according to claim 13, wherein the kinase affected is tyrosine kinase.

15. The method according to claim 13, wherein the kinase affected is ROK-I, ROK-II, PKA, PKC, CAM Kinases, GRK-2, GRK-3, GRK-5 or GRK-6.

16. A method of treating a condition comprising administering to a subject in need of treatment a safe and effective amount of a 6-aminoisoquinoline derivative according to claim 1, wherein the condition is selected from the group consisting of eye disease, bone disorder, obesity, heart disease, hepatic disease, renal disease, pancreatitis, cancer, myocardial infarct, gastric disturbance, hypertension, fertility control, nasal congestion, neurogenic bladder disorder, gastrointestinal disorder, and dermatological disorder.

17. The method of claim 16, wherein the condition comprises eye disease.

18. The method of claim 17, wherein the condition comprises glaucoma or a neurodegenerative eye disease.

19. A pharmaceutical composition comprising:
a) a 6-aminoisoquinoline derivative having the structure

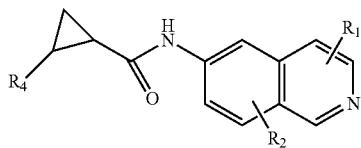

wherein $R_1$, and $R_2$ are, independently, hydrogen, hydroxyl, halogen, $C_1$-$C_4$ alkyl, $C_2$-$C_4$ alkenyl, $C_2$-$C_4$ alkynyl, amino, nitro, cyano; $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl or $C_1$-$C_4$ carboxyl; and
wherein $R_4$ is hydrogen, halogen, alkyl, alkenyl, alkynyl, alkoxy, amino, cyano, cycloalkyl, heterocycloalkyl, aryl, $C_1$-$C_4$ alkyl aryl, heteroaryl, $C_1$-$C_4$ alkyl heteroaryl, carbonyl, carbonylamino, thioalkyl, sulfonyl, sulfonylamino, acyl, or carboxyl; and
b) a carrier.

20. The composition of claim 19, wherein the carrier is selected from the group consisting of systemic and topical carriers.

21. The composition of claim 19, wherein the composition comprises about 0.001% to 10% of the 6-aminoisoquinoline derivative and 90 to 99.999% of the systemic carrier.

* * * * *